(12) United States Patent  
Miller et al.

(10) Patent No.: US 8,282,895 B2  
(45) Date of Patent: Oct. 9, 2012

(54) REAGENT CABINET SYSTEM

(75) Inventors: Jonathan Matthew Miller, Burke, VA (US); Yancy Kenan Ragin, Columbia, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 0 days.

(21) Appl. No.: 12/831,046

(22) Filed: Jul. 6, 2010

(65) Prior Publication Data

US 2011/0158865 A1    Jun. 30, 2011

Related U.S. Application Data

(60) Provisional application No. 61/242,694, filed on Sep. 15, 2009.

(51) Int. Cl.  
*B01L 1/00* (2006.01)

(52) U.S. Cl. ........ 422/500; 422/509; 137/259; 137/263; 137/374; 312/117; 312/118; 312/119; 312/122; 312/123; 312/138.1; 312/139.1; 312/209; 312/211; 312/228; 312/274

(58) Field of Classification Search .................. 422/500, 422/509; 137/259, 263, 374; 312/117, 118, 312/119, 122, 123, 138.1, 139.1, 209, 211, 312/228, 274

See application file for complete search history.

(56) References Cited

U.S. PATENT DOCUMENTS

| 4,654,308 A | * | 3/1987 | Safi et al. | 435/294.1 |
| 5,695,262 A | * | 12/1997 | Wachtler | 312/229 |
| 7,138,087 B1 | * | 11/2006 | Malkin et al. | 422/26 |

* cited by examiner

*Primary Examiner* — Jill Warden  
*Assistant Examiner* — Monique Cole  
(74) *Attorney, Agent, or Firm* — RatnerPrestia

(57) ABSTRACT

A reagent cabinet for an automated processing apparatus. The reagent cabinet has a housing, and a drawer slidably mounted in the housing. The drawer has a lower deck adapted to receive a fluid reservoir, and an upper deck located above the lower deck and adapted to receive a fluid supply container. A supply connection hose is provided to selectively connect the fluid supply container to the fluid reservoir. A reservoir connection hose is provided to selectively connect to the fluid reservoir and to convey fluid from the fluid reservoir to a downstream location outside the cabinet. A pump is mounted on the drawer. The pump is adapted to convey fluid through either the supply connection hose or the reservoir connection hose.

19 Claims, 10 Drawing Sheets

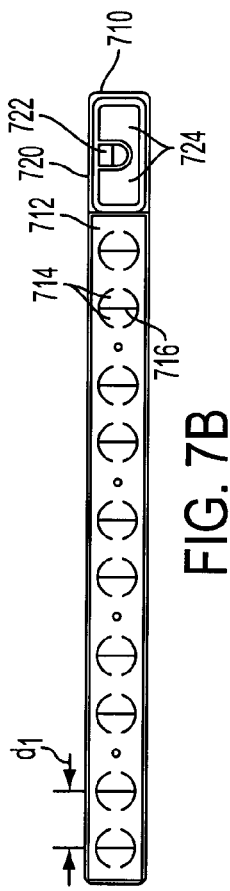
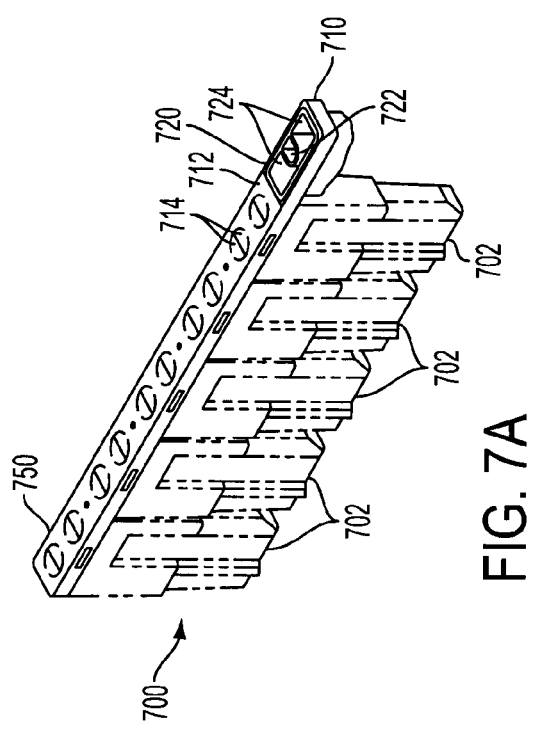
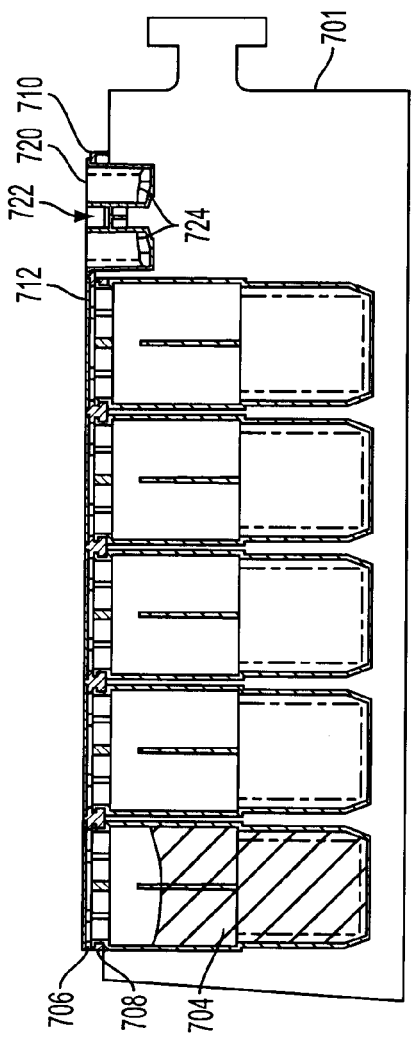
FIG. 7A
FIG. 7B
FIG. 7C

REAGENT CABINET SYSTEM

CROSS-REFERENCE TO RELATED APPLICATIONS

This application is related to and claims the benefit of U.S. application Ser. No. 12/622,162 filed Nov. 19, 2009 and U.S. Provisional Patent Application Ser. No. 61/242,694, filed Sep. 15, 2009, entitled "Automated sample processing systems and methods", and both are incorporated by reference in their entirety.

BACKGROUND

1. Field of the Art

The present disclosure relates to automated sample processing systems, and provides systems and methods that permit high-throughput specimen processing for samples that may be provided in various states of preparation.

2. Description of Related Art

Historically, biological samples being tested in the context of medical services have been processed using labor-intensive manual methods, or semi-automated methods requiring careful supervision by a laboratory technician. Such systems can be prone to operator error in many forms, such as improper testing (e.g., using an improper reagent or misreading the results), sample loss (e.g., spilling a sample), and identity loss (e.g., losing the patient name or associating the sample with the incorrect patient). While automated and semi-automated methods may help reduce labor costs and operator error, many automated systems are cumbersome to use. For example, many "automated" systems are actually only semi-automated, and may require labor-intensive pre-processing steps to transfer the input samples into a format, such as a particular sample container, that the machine can accept. Others perform a subset of processing steps but require an operator to manually perform the others, such as reagent mixing. It has also been found that existing semi-automated systems may lack safety controls, require frequent stopping for service, operate inefficiently or slowly, or have other problems or shortcomings.

There exists a need in the art for alternative automated and semi-automated processing systems, processing systems that can accept samples in various formats, and processing systems that can simultaneously process different kinds of samples. There also is a need for alternative sample processing methods. There also is a need for alternative sample processing equipment and sub-systems that may be used to assist with sample processing tasks in fully-automated, semi-automated and manually-operated systems.

SUMMARY

The present disclosure provides a number of inventions that may be used collectively, in various combinations, or alone. The following summary provided examples of such inventions, and does not limit the invention as claimed in any way.

In one exemplary aspect, there is provided a reagent cabinet for an automated processing apparatus. The reagent cabinet has a housing, and a drawer slidably mounted in the housing. The drawer has a lower deck adapted to receive a fluid reservoir, and an upper deck located above the lower deck and adapted to receive a fluid supply container. A supply connection hose is provided to selectively connect the fluid supply container to the fluid reservoir. A reservoir connection hose is provided to selectively connect to the fluid reservoir and to convey fluid from the fluid reservoir to a downstream location outside the cabinet. A pump is mounted on the drawer. The pump is adapted to convey fluid through either the supply connection hose or the reservoir connection hose.

BRIEF DESCRIPTION OF THE DRAWINGS

FIGS. 7A, 7B and 7C are isometric, top and side views, respectively, of an exemplary reagent pack and rack.

DETAILED DESCRIPTION

The present disclosure provides various exemplary embodiments of automated or semi-automated sample processing systems, methods for automated, high-throughput sample processing, control systems for coordinating and controlling the operations of a high-throughput specimen processing systems, and various devices that may be used in the foregoing sample processing systems or in other processes, devices or systems. Preferred embodiments of the invention may provide faster, more reliable, and cheaper methods and machines for high-throughput patient sample processing, but other benefits may be realized instead of or in addition to these.

Figure 1:
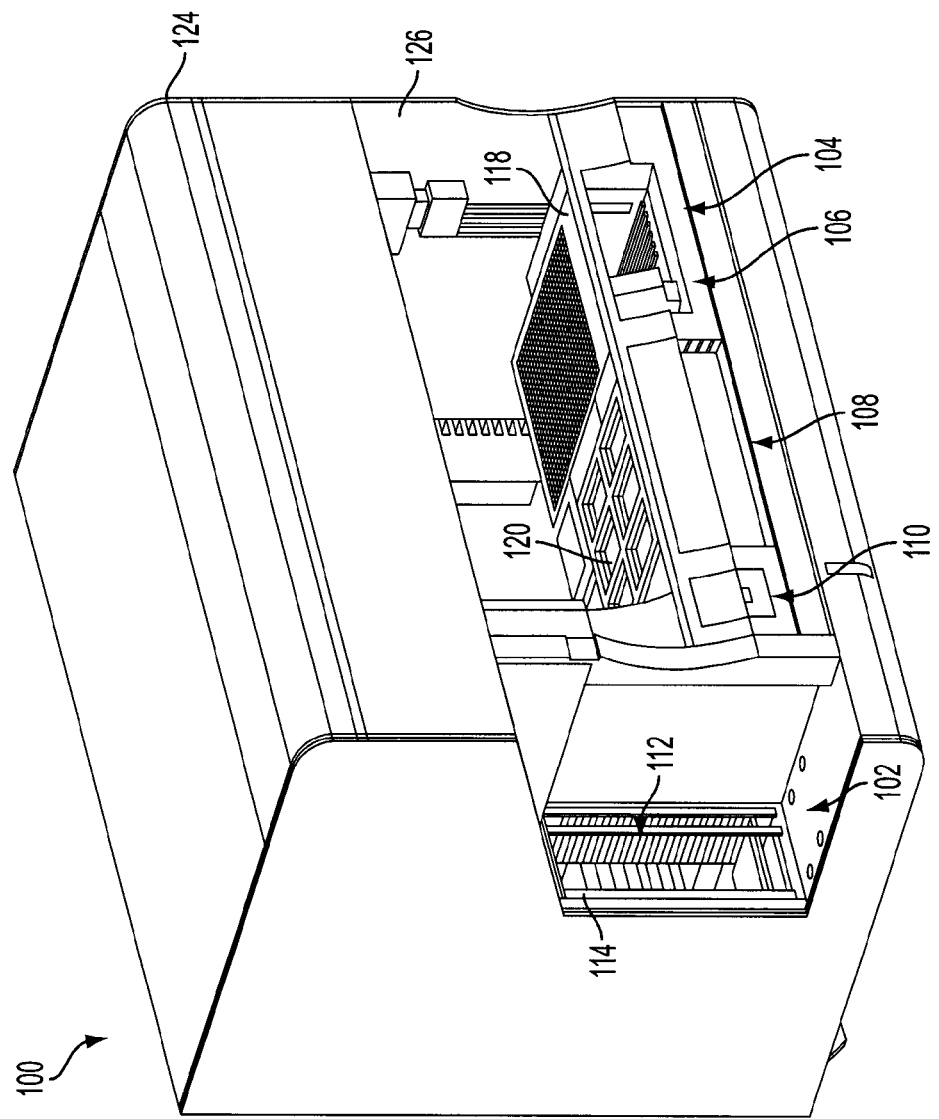
FIG. 1 is an isometric view of an exemplary automated sample processing system according to one embodiment of the invention.
Figure 2:
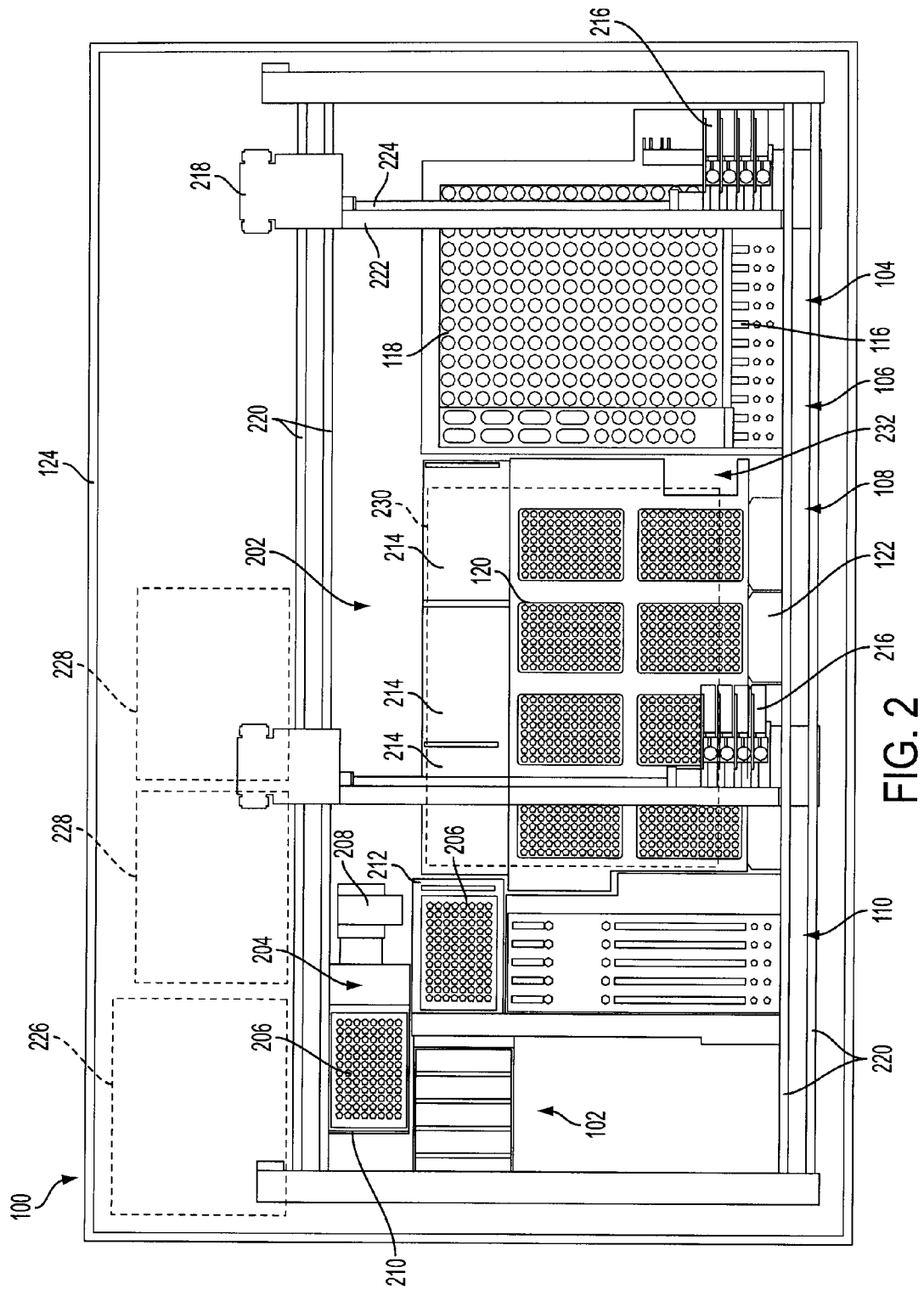
FIG. 2 is a schematic top plan view of the embodiment of FIG. 1, with the bottom of the figure corresponding to the front of the machine.
Figure 3:
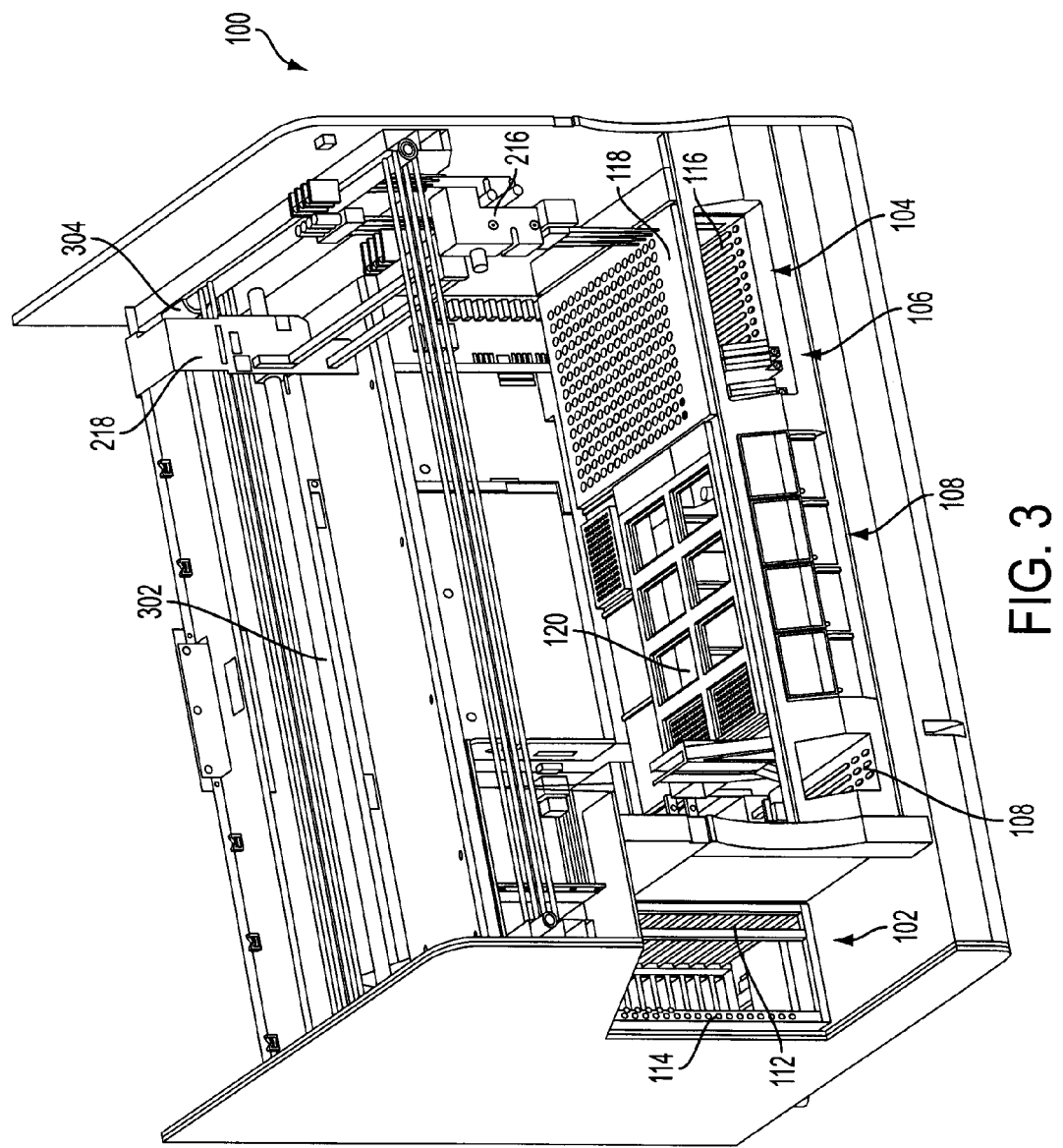
FIG. 3 is an isometric view of the embodiment of FIG. 1, shown with certain exterior panels removed to better illustrate the structure.

FIGS. 1-3 provide various views of an exemplary automated system in the form of an analytical system ("AS") 100. FIG. 1 is an isometric view of the AS 100 showing the device with its exterior coverings in place. FIG. 2 is an overhead schematic view of the AS 100, generally showing the layout of various internal parts. FIG. 3 is an isometric view with various panels and covers removed to better illustrate the internal parts. This embodiment of an AS 100 may be configured to perform an assay on patient samples to determine, for example, the presence or absence of viral DNA. For example, exemplary systems may be able to perform assays for rapid and sensitive detection of high-risk human papillomavirus ("HPV") types in clinical specimens. Assays associated with such HPV tests include, for example, those known in the digene eHR HPV DNA Test, the digene eHR HPV 16, 18/45 DNA Test, the Hybrid Capture 2 assay, and the Next Generation Hybrid Capture® Assay protocol available from QIAGEN Gaithersburg, Inc. of Gaithersburg, Md. ("Qiagen"). Steps in such an assay may include sample loading, target nucleic acid denaturation, probe hybridization, target capture, signal production, signal detection and assay result reporting. Samples used in such assays may be processed from a so-called "pap smear" sample, from cervical cell samples taken into a sample collection medium such as those described in U.S. provisional application Ser. No. 61/108,687 filed Oct. 27, 2008, U.S. provisional application Ser. No. 61/174,848, filed May 1, 2009, U.S. patent application Ser. No. 12/605,540, filed Oct. 26, 2009, or U.S. patent application Ser. No. 12/605,605, filed Oct. 26, 2009, (each of which is incorporated by reference herein), or from any other source of patient cells.

Embodiments of an AS 100 may provide high throughput screening assays, and may process samples for HR HPV screening, Reflex 16 18/45 Genotyping, CT/GC, Group B Step, Trichomonas, Vaginosis, Cancer Dx, and so on. Exemplary assays that may be performed in embodiments of the invention are described in U.S. Provisional Application Ser. No. 61/045,952, filed Apr. 17, 2008, entitled "COMPOSITIONS, METHODS, AND KITS FOR DETERMINING NUCLEIC ACID"; U.S. Provisional Application Ser. No. 61/113,841, filed Nov. 12, 2008, entitled "COMPOSITIONS, METHODS, AND KITS FOR DETERMINING NUCLEIC ACID," U.S. Provisional Application Ser. No. 61/122,621 filed Dec. 15, 2008 entitled "AUTOMATED HPV ASSAY AND SYSTEM"; 61/147,623, filed Jan. 27, 2009, entitled "ISOTHERMAL HELICASE DEPENDENT MULTIPLEX ASSAY FOR DETECTION OF CHLAMYDIA TRACHOMATIS AND NEISSERIA GONORRHOEAE WITH FLUORESCENCE ENDPOINT DETECTION," U.S. Ser. No. 12/426,076, filed Apr. 17, 2009; U.S. Provisional Application Ser. Nos. 61/108,687, filed Oct. 27, 2008, entitled "NOVEL FAST RESULTS HYBRID CAPTURE ASSAY"; 61/179,848, filed May 1, 2009, entitled "NOVEL FAST RESULTS HYBRID CAPTURE ASSAY"; U.S. patent application Ser. No. 12/605,540, filed Oct. 26, 2009, entitled "Fast Results Hybrid Capture Assay and System"; Ser. No. 12/605,605, filed Oct. 26, 2009, entitled "Fast Results Hybrid Capture Assay On An Automated Platform"; U.S. Pat. No. 6,228,578, U.S. Provisional Application No. 61/180,821; Tong et al., "Development of isothermal TaqMan assays for detection of biothreat organisms," BioTechniques Vol. 45, 543-557 (2008); Motré et al. "Enhancing helicase-dependent amplification by fusing the helicase with the DNA polymerase," Gene Vol. 420, 17-22 (2008); Chow et al., "Application of Isothermal Helicase-Dependent Amplification with a disposable Detection Device in a Simple Sensitive Stool Test for Toxigenic *Clostridium difficile*," J. Mol. Diagnostics. Vol. 10 (5), 452-458 (2008); Li et al., "Primase-based whole genome amplification," Nucleic Acids Research 36(13): e79 (2008); Goldmeyer et al., "Identification of *Staphylococcus aureus* and Determination of Methicillin Resistance Directly from Positive Blood Cultures by Isothermal Amplification and Disposable Detection Device," J. Clin. Microbiol. Vol. 46, 1534-1536 (2008); Kong et al., "New isothermal molecular diagnostic platforms," IVD Technology November issue (2007); Goldmeyer et al., "Development of a novel one-tube isothermal RT-tHDA platform for rapid RNA detection," J. Mol. Diagnostics. Vol. 9, 639-644. (2007); Xu et al., "Simultaneous amplification and screening of whole plasmids using the T7 bacteriophage replisome," NAR 34(13): e98 (2006); An et al., "Characterization of a Thermostable UvrD Helicase and its Participation in Helicase Dependent Amplification," The Journal of Biological Chemistry Vol. 280, 28952-28958 (2005); and Vincent et al., "Helicase Dependent Isothermal DNA Amplification," EMBO reports Vol. 5, 795-800 (2004), the contents of which are hereby incorporated by reference in their entireties.

Additionally, though laboratory protocols are often quite diverse in their particular steps, many generally rely on various common underlying operations, such as the addition of reagents, mixing, incubating, and so on. Embodiments of the invention described herein may be adapted to provide the ability to perform a diverse set of common laboratory operations, with different systems readily constructed from combinations of system components described herein to perform at least a subset of the steps required in virtually any protocol. In addition to or instead of measuring a sample characteristic, embodiments of the invention may be adapted to provide a tangible output in any suitable output format, including multi-well formats, outputs to a membrane or blotting paper, bacterial, yeast or mammalian cell culture plate, and so on. The systems provided herein may be utilized, for example, for high-throughput preparation of DNA, RNA, protein, plasmids, chromosomes, antibodies, or organelles. Other systems may be used to perform all or part of methods such as: transformation; mating (e.g., of yeast, nematodes, or other small organisms); cloning; dot blotting (for DNA, RNA, protein, enzyme, etc.); mutagenesis; preparation for sequencing; nucleic acid amplification; primer synthesis; ELISA; enzyme assays; X-gal staining; immunohistochemistry; immunofluorescence; sample fixing; flow cytometry; in-situ hybridization; in vitro transcription and/or translation; sample purification from agarose; peptide synthesis; combinatorial library preparation; and so on. Processes using embodiments of the invention may employ samples of virtually any origin including, for example: prokaryotic cells; eukaryotic cells; tissue samples from multicellular organisms; whole organisms (e.g., flies, worms, or other similarly small organisms); conditioned media; environmental samples; and so on. Exemplary protocols that may be performed include those shown in the texts "Molecular Cloning: A Laboratory Manual" (Third Edition, Cold Spring Harbor Press) or "Condensed Protocols From Molecular Cloning: A Laboratory Manual" (First Edition, Cold Spring Harbor Press), the disclosures of which are hereby incorporated by reference in their entireties. In addition, as explained below, the AS 100 may be configured and programmed to perform various different assays essentially at the same time, where multiple different sample types are input into the system at the same time.

A central control unit (CCU) may be used to control and/or monitor the AS 100. The CCU may be a dedicated software controller for the AS 100, a multi-system controller that monitors or oversees operation of the AS 100 an upstream pre-analytical system ("PAS") or other devices, or any combination of control, monitoring or reporting systems. An example of a pre-analytical system that may be used to prepare samples, such as samples provided in standard 96-well sample plates described below, is described in U.S. application Ser. No. 12/588,304, filed on Oct. 9, 2009, which is incorporated herein by reference. An exemplary CCU may provide a processing interface between the AS 100 and the PAS. For example, a CCU may be combined with an AS 100 and a PAS to perform all of the steps necessary to pre-process and test a sample according to the Hybrid Capture 2 or Next Generation Hybrid Capture® protocols. An exemplary CCU may have features such as those described in U.S. Application No. 61/262,497 filed Nov. 18, 2009, which is incorporated herein by reference in its entirety.

The exemplary AS 100 is a generally self-contained unit having various input and output locations at which an operator can provide supplies and remove waste and processed samples. The AS 100 may be enclosed in a housing 124, which may have a window 126 through which an operator can observe the operation of the machine. While the shown AS 100 is a stand-alone unit, alternative embodiments may partition various parts of the machine into separable modules, or integrate the machine into a larger processing system.

In the exemplary embodiment, the AS 100 includes a first sample bay 102, a second sample bay 104, a control bay 106, a pipette tip input 108, a reagent bay 110, and one or more solid or liquid waste outputs (not shown). The functions of these various inputs and outputs are described in more detail below. The AS 100 also may include a suitable electrical interface (not shown) for connecting to a CCU that controls the device. Of course, the CCU, or various parts of it, may be integrated into the AS 100 itself, in which case the AS 100 may be provided with a human interface to receive operating instructions and/or display system status. Such an interface may include various interface elements known in the art, such as a monitor, touch-screen monitor, keyboard, mouse, microphone, speaker, barcode reader, and so on. While the shown arrangement of inputs and bays has been selected for this embodiment, it will be understood that other arrangements may be used in other embodiments.

The first sample bay 102 is adapted to receive samples, such as liquid-based cytology (LBC) samples, that are provided as collections of samples on sample plate. Each sample plate may include one or more patient samples. The first sample bay 102 has a number of vertically-stacked tracks 112 (e.g., fifteen tracks), each of which receives one plate. In the exemplary embodiment, the first sample bay 102 receives plates from a user, and returns the plates to the user for removal once processing is complete. The tracks 112 preferably can be individually loaded and unloaded with plates during operation of the machine, to provide a substantially continuous supply of first samples for processing.

To prevent confusion, lights 114 or other indicators may be provided adjacent each track 112 to indicate the status of the plate associated with that track 112. For example, a green light may indicate that a track is free to receive a plate, or that a plate in that track is free to be removed. An orange light may indicate that the plate in that track is queued for processing and can not be removed. A red light may indicate that an empty track should not be filled with a plate because a plate currently being processed is intended to be replaced in that particular track. Other colors and flashing lights may be used to indicate additional status situations.

Locks also may be provided on the tracks 112 to prevent improper removal or insertion of plates. In addition, a door (not shown) may be provided to enclose the first sample bay 102 when it is not being used. It will be appreciated that many variations may be made to the foregoing exemplary embodiment. For example, the first sample bay 102 may comprise separate plate input and output locations, the tracks may be arranged in different orientations, and so on. These and other variations may also be applied to the other tracks, supplies and loaded components described below.

Figure 4:
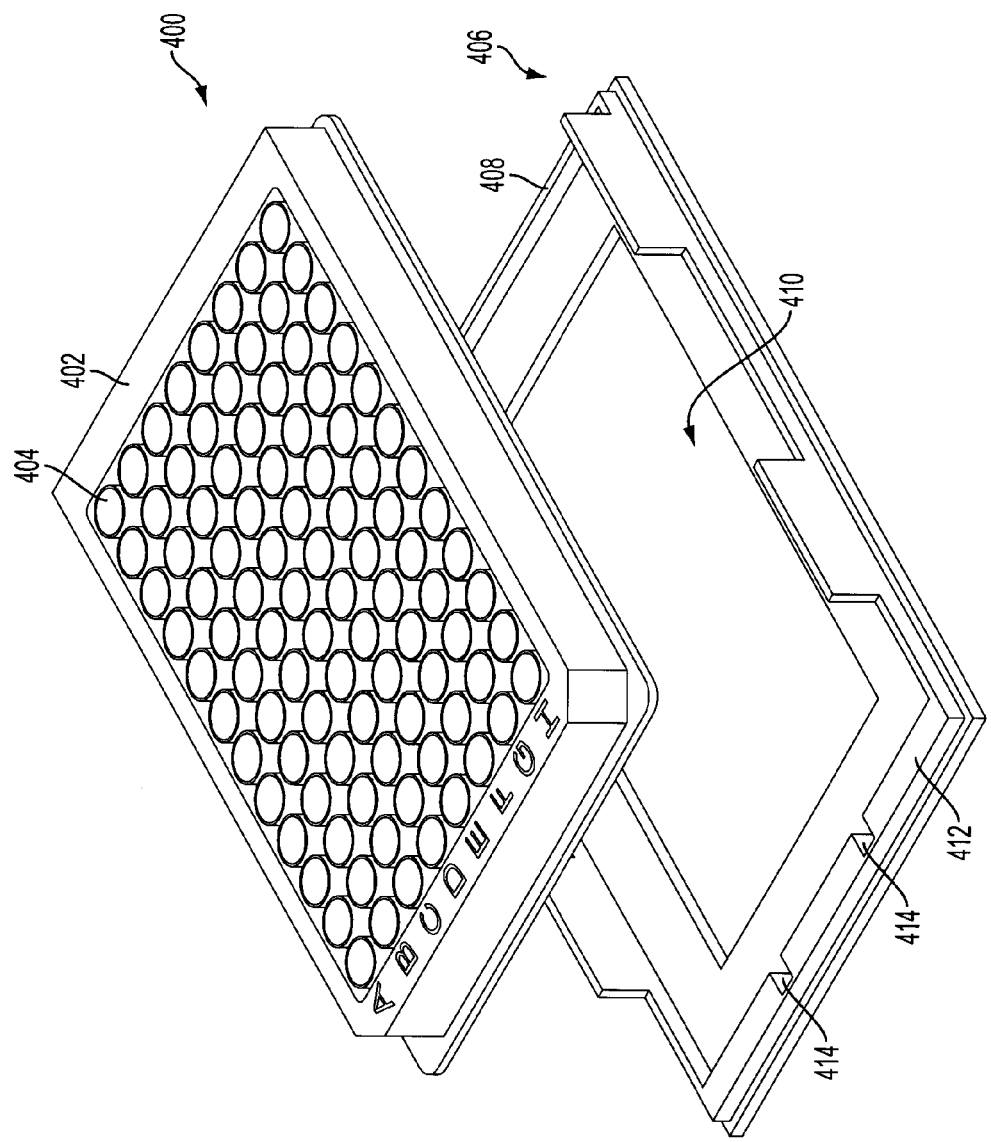
FIG. 4 is an isometric view of an exemplary multi-well plate.

An example of a first sample plate that may be used in the first sample bay is shown in FIG. 4. In this embodiment, the plate comprises a standard 96-well plates 400, such as shown in FIG. 4, may be used to supply up to ninety-six samples each at the first sample bay 102. As shown in FIG. 4, each 96-well plate 400 includes a plate frame 402 and a number of wells 404. A separate sample may be placed in each well, and a plate sealer may be used to seal the plate to help prevent cross-contamination and evaporation. An exemplary 96-well plate is the Greiner 96-well microplate available from Greiner Bio-One GmbH of Frickenhausen, Germany. These and other plates, as well as plate sealers, are well-known in the art and need not be described here. If the chosen sample plate lacks structural features by which it can be manipulated as desired by the AS, the sample plates may be mounted in carriers, such as carrier 406, that hold the plate and provide manipulation points to enhance the AS's ability to manipulate the plate. The shown carrier 406 includes a perimeter frame 408 to retain the plate 400, an opening 410 to provide access to the bottom of the plate 400, and a manipulation track 412 having openings 414 to receive a toothed moving arm. An exemplary moving arm (not shown) may have teeth that fit into the openings 414 to push and pull the carrier 406 and plate 404. Such devices are known in the art and available, for example, from Stratec Biomedical Systems AG of Germany.

Though this example is described using 96-well plates, embodiments may readily be adapted for processing samples in another multi-well plate formats (e.g., 6-well, 12-well, 24-well, 48-well, 384-well or 1536-well plates, or other multi-well plate formats).

Figure 5:
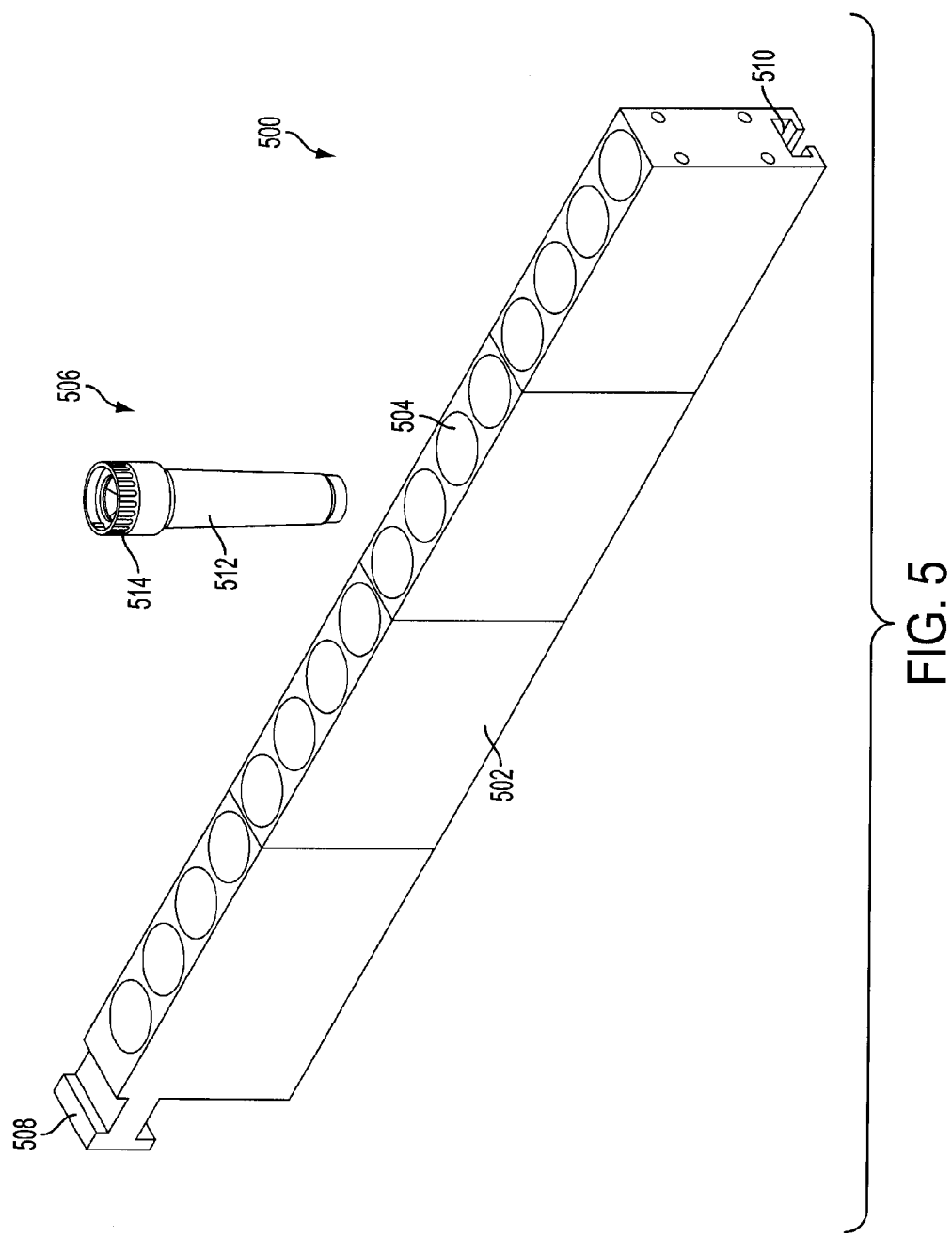
FIG. 5 is an isometric view of an exemplary sample rack and an exemplary sample container.

The AS 100 preferably also includes a second sample bay 104 to receive samples which may be in a different format than those provided in the first sample bay 102. In the exemplary embodiment, the second sample bay 104 comprises a series of side-by-side tracks 116 that are located remotely from the first sample bay 102. These tracks 116 are adapted to receive samples provided on a sample rack, such as shown in FIG. 5. The rack 500 may be a conventional design, having a rack body 502 with multiple wells 504 that are each adapted to hold a sample container 506. A handle 508 may be provided at one end of the rack 500, and a groove 510 may be provided to receive the track 116 to guide and orient the rack 500 as it is installed. Such rack and track systems are known in the art, and need not be described in further detail herein. While the shown rack 500 holds samples in a linear array (i.e., in a single row), alternative racks may hold sample containers in a two-dimensional array. The wells in such an array may be in a square pattern (as in the sample plate 400), staggered, in a radial pattern, or in any other suitable pattern. An example of a sample container rack having a two-dimensional well array is shown in U.S. application Ser. No. 12/622,150 entitled "Sampling Devices and Methods" filed on Nov. 19, 2009, which is incorporated herein by reference. Such a rack may hold a single kind of sample, or multiple different sample types.

The second sample bay 104 may include locks and/or status indicators (such as lighted LEDs) to help regulate the insertion and removal of samples. If desired, a door (not shown) may be proved over the second sample bay 104. The racks 500 preferably can be individually loaded and unloaded during operation of the machine, to provide a substantially continuous supply of second samples for processing.

The sample rack 500 may hold samples provided in one more different kinds of sample container. For example, the rack 500 may hold samples provided in the shown exemplary sample tube 506. The sample container 506 may comprise a tube body 512 and a removable cap 514. Many different kinds of sample container 506 may be used. For example, the sample container 506 may comprise a liquid-based cytology container for holding cervical samples, a urine vial, a blood vial, and so on. Many different shapes and sizes of such containers are known, and the rack 500 can be modified to fit any typical container, as desired.

The sample rack 500 may be modified, as desired, in other embodiments. For example, the rack 500 may have one or more barcodes on it, and may have cutouts along the side of each well 504 so that a barcode reader can scan a barcode provided on each sample container 506 as the rack 500 is being moved along the track 116. Barcodes may be used to identify each sample and associate each sample with a rack position, and double-check that each sample is intended to be used in the assay being conducted in the AS 100. Other uses for barcoding may also be apparent to those of ordinary skill in the art.

The rack 500 and sample containers 506 also may include features, such as pierceable caps and magnets on the rack and magnetic brushes in the containers, to facilitate the pipetting operations described herein. Examples of such magnetic features are described in U.S. application Ser. No. 12/622,150 entitled "Sampling Devices and Methods" filed on Nov. 19, 2009. Another exemplary feature that may be used with the second sample bay 104 is a retainer panel 118 located above the tracks 116 and racks 500. The retainer panel 118 has openings above each sample location when the racks 500 are installed, to allow access to each sample container. In addition, the retainer panel 118 may be modified to hold the sample containers in place to prevent pipette tips (or other devices that may be inserted into and withdrawn from the sample containers) from lifting the sample containers out of the racks 500. Any suitable construction for a retainer panel 118 may be used, and in one embodiment, the retainer panel 118 comprises a stepped or ramped design that helps reduce the likelihood that sample containers will be contaminated as they are installed or removed from the second sample bay 104. Examples of such a retainer panel 118 are described in U.S. application Ser. No. 12/622,140entitled "Sample Vial Retainer" filed Nov. 19, 2009. The foregoing two applications are incorporated herein by reference in their entireties.

In one exemplary embodiment, a process for loading racks 500 having samples containers may include sliding the racks into the second sample bay 104, and using a CCU and scanner to scan barcodes on each rack and/or sample container as they are being slid into place. If all of the barcodes are not successfully scanned, the rack is removed, and the samples may be rearranged to better present their barcodes to the scanner, or they may be manually scanned or entered into the system by other means, such as manual alphanumeric input. Once the data for each sample and rack is captured by CCU, the CCU determines the work schedule for each sample (e.g., the assays to be run, and whether a subsequent reflex assay will be performed is a positive result is obtained). The work schedule may be obtained from a CCU, user input, an indicator associated with a sample, other known means, or combinations of the foregoing. For example, if a sample is provided for which the software controller has not received a work order, a user may be prompted to indicate whether an assay is ordered. The CCU then confirms that each sample calls for the assays or tests for which the AS 100 is configured (e.g., with respect to the reagents and buffers), and confirms that sufficient system resources are available to conduct the necessary steps before initiating processing.

Figure 6:
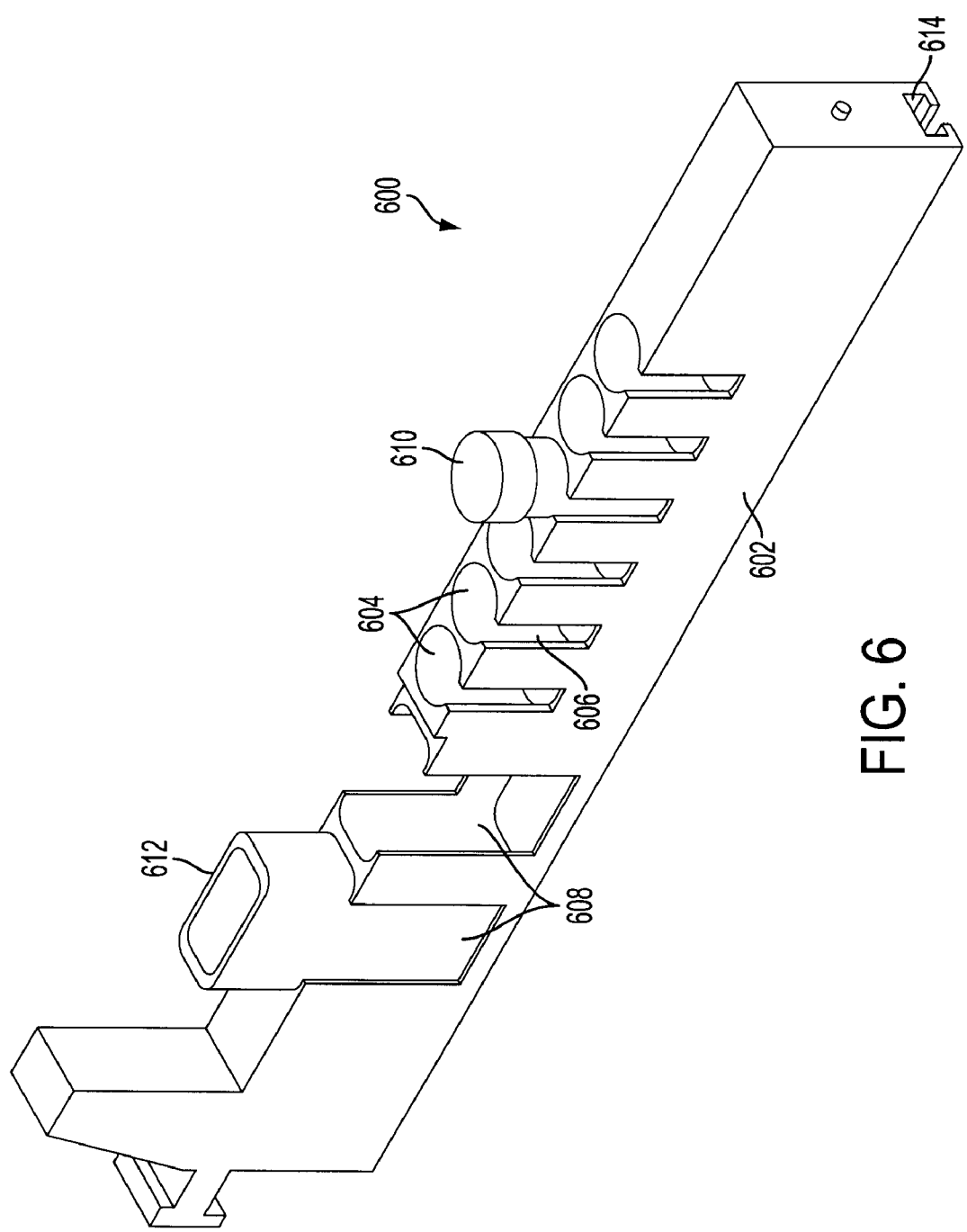
FIG. 6 is an isometric view of an exemplary control vial, and exemplary oil container, and an exemplary rack for holding the control vial and oil container.

The exemplary control bay 106 is located next to the second sample bay 104, although other locations may be used in other embodiments. The control bay 106 is provided for the addition of control and/or calibration samples that may be selectively used by the AS to confirm proper operation. Examples of control and calibration regimes are described in more detail below. The control and calibration samples can be provided in any suitable form. For example, FIG. 6 illustrates an exemplary control rack 600 that may be used to provide control and calibration samples that are provided in vials similar to the sample container 506 described above. In particular, the control and calibration samples may be provided with pierceable caps, so that the operator is not required to open them before placing them in the machine. While pierceable caps are preferred in some instances, other embodiments of the AS 100 may use containers with machine-removable caps (such as twist-off caps or pushcaps) that are automatically removed to process the container's contents. Examples of twist-off caps and pushcaps include those shown in U.S. application Ser. No. 12/588,304 filed Oct. 9, 2009 (showing a decapping unit to remove twist-off caps) and U.S. application Ser. No. 12/616,899 filed Nov. 12, 2009 (showing a machine-removable pushcap). The foregoing references are incorporated herein by reference in their entireties. In still other embodiments, the various containers may simply use hand-removed caps or covers over the various samples, reagents, controls, calibrators and so on.

In the exemplary embodiment, the control rack 600 is similar to the second sample rack 500 described above. In particular, the control rack 600 includes a rack body 602 having multiple control wells 604, each of which includes a slot 606 through which a barcode on each control can be read. Barcoding can be used to identify the controls, ensure they are properly positioned, and so on. Barcodes between each adjacent pair of wells 602 may be used to associate each control with a particular well. A reader (not shown) located at one side of the control bay 106 to project a reading beam along the width of the bay 106 can read each barcode as the rack 600 is installed. The control racks 600 also may include a track 614, like the track 510 on the sample rack 500, to orient and guide the rack 600 in the AS 100.

As shown, one exemplary embodiment of a control rack 600 may include six control wells 604. In this embodiment, two of the wells are used for positive controls 610, two are used for negative controls, and two are used for calibrators. To further reduce the likelihood of error, the containers in which the controls and calibrators are provided may be color-coded to match particular designated wells 604. The control rack 600 also may hold reagents, patient samples, or other consumables used by the AS 100. For example, the control rack 600 may include two additional wells 608 adapted to receive oil packages 612. Oil in these packages 612 may be used, for example, to cover the patient samples as they are processed to help reduce evaporation during incubation, testing, processing or storage. Reagents also may be provided in the control rack 600. The control racks 600 preferably can be individually loaded and unloaded during operation of the machine, to provide a substantially continuous supply of controls, calibrators, oil and so on to the machine.

Locks or status indicators may be provided to help regulate when control racks 600 may be inserted into and removed from the control bay. Also, a retainer panel 118, such as described above, may be positioned over the control bay to retain controls, calibrators, oil packages, and whatever other containers may be used in the control racks 600.

An exemplary process for loading controls and calibrators into the AS 100 may include loading controls, oil and calibrators onto racks 600, sliding one or more filled control racks 600 into the control bay 106, and scanning them as they are being slid into place. A CCU checks the scanned barcode data, and determines whether the controls, calibrators and oil are valid (e.g., not expired, not previously used and depleted, the proper controls/calibrators/oil for the particular tests being run, etc.). The CCU also may initiate a test count to determine the number of tests that can be performed using the supplies, optimize the number of tests, store the number of test for use during processing, and display the number of tests to an operator on a graphical user interface. Of course, other loading processes may be used in other embodiments.

Referring to FIGS. 1 and 3, the pipette tip input 108 is provided to load unused pipettes into the AS 100. This input 108 may be on the front of the machine, but other locations are possible in other embodiments. The pipette tip input 108 may comprise any suitable arrangement for loading unused pipette tips into the AS 100. In the shown embodiment, the pipette tip input 108 comprises multiple drawers that hold pipette tip racks. Each rack includes a number of holes into which unused pipette tips are placed. When the drawers are closed, the pipette tips are oriented vertically, and accessible by one or more automated pipettors through one or more openings 120. If desired, different kinds of pipette tips may be provided in different drawers. For example, where different assays to be run simultaneously require different pipette tips, tips appropriate for both assays may be loaded and the system programmed to use the appropriate tips for each assay. The design of suitable pipette tip drawers is known to persons of ordinary skill in the art and need not be described herein. If desired, the drawers may be provided with locks and indicators, such as LED lights 123, to ensure that the drawers are not opened as pipettes are being withdrawn from the racks. Such lights also may indicate status, such as: locked or unlocked, ready for loading, empty, or in-use. A CCU associated with the AS 100 also may be programmed to indicate to the user when all of the drawers are full, indicate the number of tests that can be run with the available tip supply, provide real-time monitoring of the drawers, and so on.

The reagent bay 110 also may be located on the front of the AS 100, or elsewhere as desired. Like the second sample bay 104, the reagent bay 110 may comprise a number of rails adapted to receive reagents provided on racks. To ensure that racks are not improperly loaded, the racks for the second sample bay 104, control bay 106, and reagent bay 110 may be constructed such that they are not interchangeable (e.g., by providing different track shapes for each kind of bay and rack). Each track may have a lock or a light to help regulate access to the racks. For example, a multicolor LED may be provided to illuminate green to signal that a rack is empty and unassigned to the system resources, red to signal that a rack is loaded but not yet assigned to the system resources, or orange to indicate a loaded and properly assigned reagent rack.

Referring now to FIGS. 7A-7C, reagents may be provided in individual containers or in one or more reagent packs 700. The shown exemplary reagent pack 700 includes multiple reagent reservoirs 702, each of which contains a reagent 704. A single reagent pack 700 may include all reagents necessary to perform a given assay, but this is not required. A seal 706 covers openings 708 at the top of each reagent reservoir 702. The seal 706 may be made of a pierceable material, such as a foil, plastic film, etc. that can be penetrated by a robotically actuated pipette to gain access to the reagents 704 during use. Each reagent reservoir 702 may be sized to receive one or more pipettes, such as the shown embodiments which are sized to receive two pipettes at a time. If mixing of reagents is necessary, an automated pipettor may draw reagents from one reservoir and mix them with reagents in another reservoir. In-place mixing to ensure the reagents are homogeneous may also be done using shaker or, more preferably, by repeatedly drawing reagent into a pipettor and depositing it back into the reservoir (i.e., mixing by so-called "pipetting action").

The reagent pack 700 is held in a reagent rack 701 that is adapted to slide into the reagent bay 110. The reagent rack 701 may be constructed in any suitable way. For example, in a preferred embodiment the rack 701 is built similarly to the racks described above with respect to FIG. 5 or 6, with a track to orient and hold the rack 701 as it is slid in and out of a corresponding track in the reagent bay 110, a bar code to identify the specific rack 701, and one or more barcodes to identify the reagent reservoirs being loaded into the AS 100. The racks 701 preferably can be individually loaded and unloaded during operation of the machine, to provide a substantially continuous supply of reagents. Also, reagent packs 700 having reagents for multiple different assays may be loaded at the same time, if desired.

The reagent reservoirs 702 are affixed to a common frame 710. Alternatively, the reagent packs 700 may be made of a single integrally molded piece comprising multiple reagent reservoirs 702 and an integral frame 710. The frame 710 includes a flexible cover 712 that covers one or more of the reagent reservoirs 702. The flexible cover 712 is situated above the seal 706 in the depicted embodiment, though other spatial arrangements are contemplated. For example, a flexible cover may be situated below a seal, or a reagent reservoir may include a flexible cover or a seal, but not both. The flexible cover 712 defines flexible flaps 714 above each reagent reservoir 702, with each pair of flaps adapted to accommodate insertion of a pipette tip. The flexible flaps 714 provide partial re-covering of the reagent reservoirs 702 after a pipette tip is inserted and removed, helping to reduce the rate of evaporation and decrease the likelihood of reagent contamination. Additionally, the flexible flaps 714 may sweep the sides of a pipette tip as it is withdrawn, helping to dislodge any liquid that is clinging to the outside of the pipette tip and cause such liquid to drop back into its reagent reservoir 702. Each flexible flap 714 may include a small notch or indentation 716 at the mid-line of flexible cover 712. The indentation 716 tends to keep flexible flap 714 centered on a pipette tip as it is inserted or removed from the reagent reservoir 702.

In the depicted embodiment, the rightmost reagent reservoir 702 is provided with a mixing station 720. The mixing station 720 comprises a concentrated reagent reservoir 722 and a well 724 that may surrounds or partially-surround the concentrated reagent reservoir 722. A cover, such as a pierceable foil cover (not shown), may be provided over the mixing station. Initially, a concentrated reagent is contained in the concentrated reagent reservoir 722. Some or all of the concentrated reagent can then be drawn from concentrated reagent reservoir 722 and mixed with a diluent in the well 724. The diluent can be provided in the well 724, or dispensed there from one of the reagent reservoirs 702 or from another source. For example, in one embodiment, the diluent is provided in the right-most reagent reservoir 702. In this embodiment, at least some of the reagents may be prepared by withdrawing some of the diluent from the reservoir 702 and depositing this diluent into the well 724. Next, the concentrated reagent is drawn from the concentrated reagent reservoir 722, deposited into the well 724, and mixed with the diluent by, for example, pipetting action or shaking the reservoir. This partially-diluted concentrated reagent can then be drawn into the pipettes, deposited into the right-most reagent reservoir 702, and mixed again to fully dilute the concentrated reagent. The use of the foregoing or similar processes is expected to save a significant amount of operator time over conventional systems, which typically require manual mixing of reagents before operation. Additionally, automated mixing of reagents may be performed in advance of the expected time for commencement of sample processing, such that the machine will be ready to commence sample processing without incurring any delay for reagent mixing. For example, reagent mixing may be started at the end of a work shift, at a pre-set time during a period of inactivity, manually at the start of a work shift, or in response to another triggering event.

In an exemplary embodiment, the reagent reservoirs 702 may contain a denaturation reagent, detection labeled antibodies, bead suspensions, detection reagents, diluents, and/or nucleic acid probes (such as RNA, DNA, and synthetic nucleic acid analogues, etc.). When a reagent comprises a suspension such as magnetic beads or another reagent susceptible to settling or separation, periodic mixing may be performed by pipetting action or other known means. For example, an initial mixing procedure involving multiple cycles of aspiration and dispensing may be performed when the reagent pack 700 is first put into use or is used after an extended period of non-use. Subsequently, additional mixing, which may be less extensive than initial mixing, may be performed prior to each use or at a predetermined interval (e.g., after a fixed period of time has elapsed since the last time the reagent was mixed or used). To minimize inefficiencies, such intermediate mixing may be scheduled while other processes are running.

Because the volume of a reagent will decrease as the reagent is consumed, the volume aspirated and dispensed during pipettor mixing can be varied accordingly to ensure adequate mixing of the remaining volume. For example, aspiration volume may be 20% of the calculated remaining reagent volume—i.e., volume=(number of tests remaining)* (volume per test)*0.20. A lower boundary on the aspiration volume can be used to ensure that the volume is sufficient for adequate mixing. Accommodating this lower boundary on aspiration volume may be accomplished using a reagent reservoir that is "overfilled" such that there is always sufficient volume remaining for adequate mixing to be performed. Alternatively, resuspension may not be attempted if the reagent volume remaining is below a defined cutoff volume; rather, if resuspension is required (e.g., due to elapsed time), it would not be attempted and instead the reagent pack would have to be discarded. In still another embodiment, reagent from a nearly expired pack that can no longer be suitably mixed may be aspirated and combined with a new reagent pack, however such a practice may be limited to circumstances in which the two reagent packs correspond to a common production lot, calibration profile, or other control variable to ensure that cross-use of reagent does not adversely affect performance. One of skill in the art can readily determine a minimum volume for aspiration/dispense to achieve sufficient mixing for a given reagent and implement reagent-conserving systems as described herein.

One or more sensors may be provided to detect the levels of the reagents 704. Known ultrasonic sensors or other kinds of sensors may be used to check the fluid levels. In addition, sensors such as light detectors located in the reagent reservoirs or in hoses downstream of the reagent reservoirs 702 may be used to determine the presence of bubbles or air pockets in the fluid.

The reagents packs 700 may be loaded into the AS 100 using any suitable process. For example, the reagent packs 700 may be brought to room temperature (if refrigerated), loaded into corresponding racks 701, slid onto a rack in the reagent bay 110, and scanned as it is slid into place. A CCU determines whether the reagent pack 700 is valid (e.g., the proper reagents for the intended assay, not expired, not previously used and consumed, etc.), and initiates a mixing sequence if the reagent pack 700 is valid. The CCU also may evaluate the reagent pack 700 to determine the number of tests that may be performed using that pack or a collection of packs loaded in the AS 100, identify a reagent use procedure to maximize the total number of tests, store the test count for use during processing, and display the test count to the operator. Of course, other loading processes may be used in other embodiments.

The housing 124 may be mounted on a carriage (not shown) that may act as a storage cabinet for supplies, and may be operatively connected to the housing 124 to provide supplies during operation. For example, the housing 124 may be mounted on a carriage that contains wash buffers and one or more storage containers for solid and liquid waste. Alternately, where no biohazardous fluid or other controlled waste are generated by the AS 100, the fluid waste can be directed to a sink. Such a carriage may be movable on casters or wheels, and locked in place using wheel locks or legs that can be lowered into engagement with the floor. The design of combined carriage and storage cabinets is known in the art, and need not be described here in detail.

The housing 124 may be mounted on a carriage (not shown) that may act as a storage cabinet for supplies, and may be operatively connected to the housing 124 to provide supplies during operation. For example, the housing 124 may be mounted on a carriage that contains wash buffers or reagents and one or more storage containers for solid and liquid waste. Alternately, where no biohazardous fluid waste are generated by the AS 100, the fluid waste can be directed to a sink. Such a carriage may be movable on casters or wheels, and locked in place using wheel locks or legs that can be lowered into engagement with the floor. The housing 124 alternatively may be operated as a bench-top unit. A bench-top unit may have all of the necessary fluid supplies and waste containers integrated into the housing 124, or fluid supplies and containers may be provided as separate units or containers.

Figure 8A:
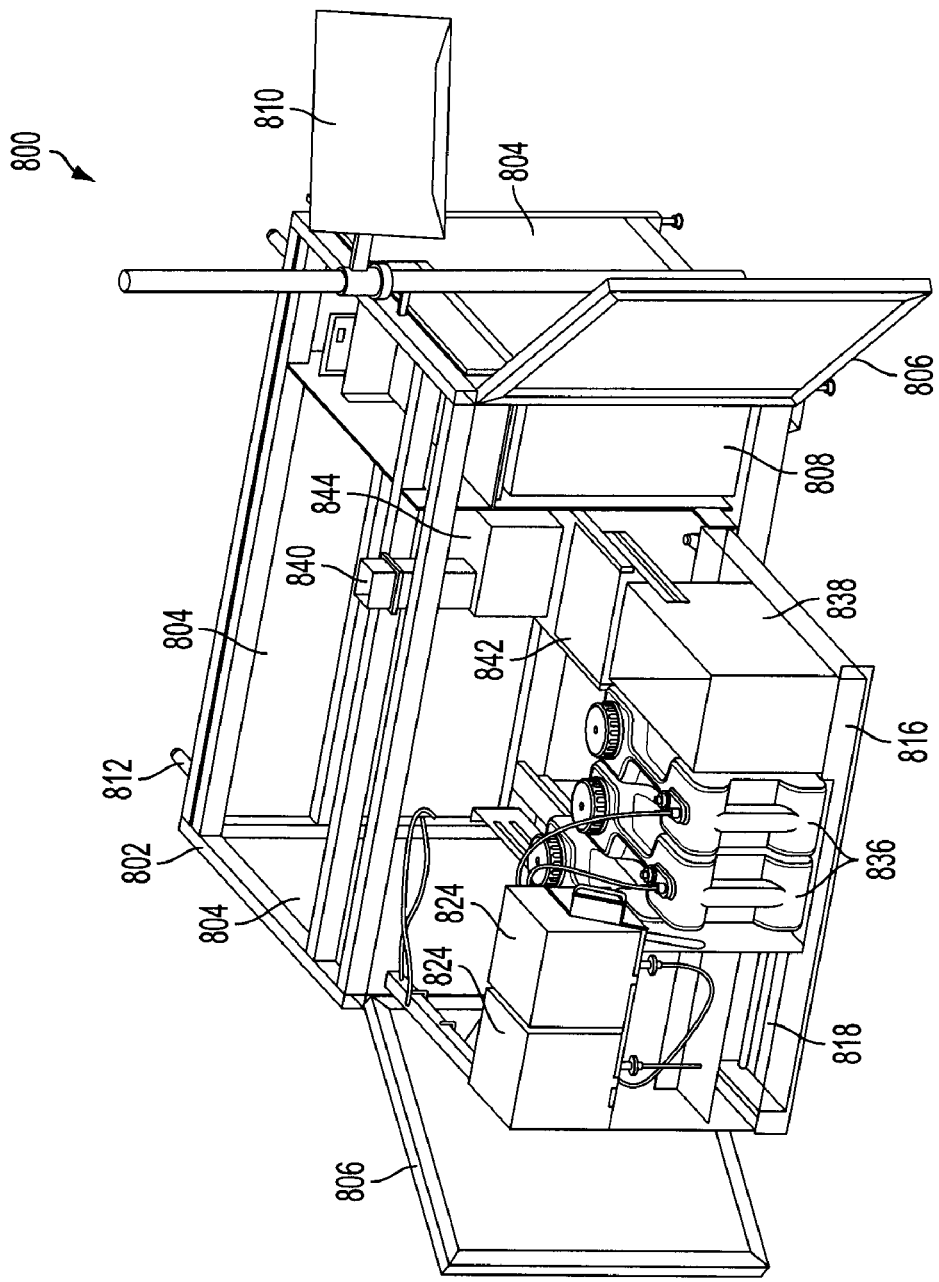
FIGS. 8A and 8B are isometric views of an exemplary cabinet.
Figure 8B:
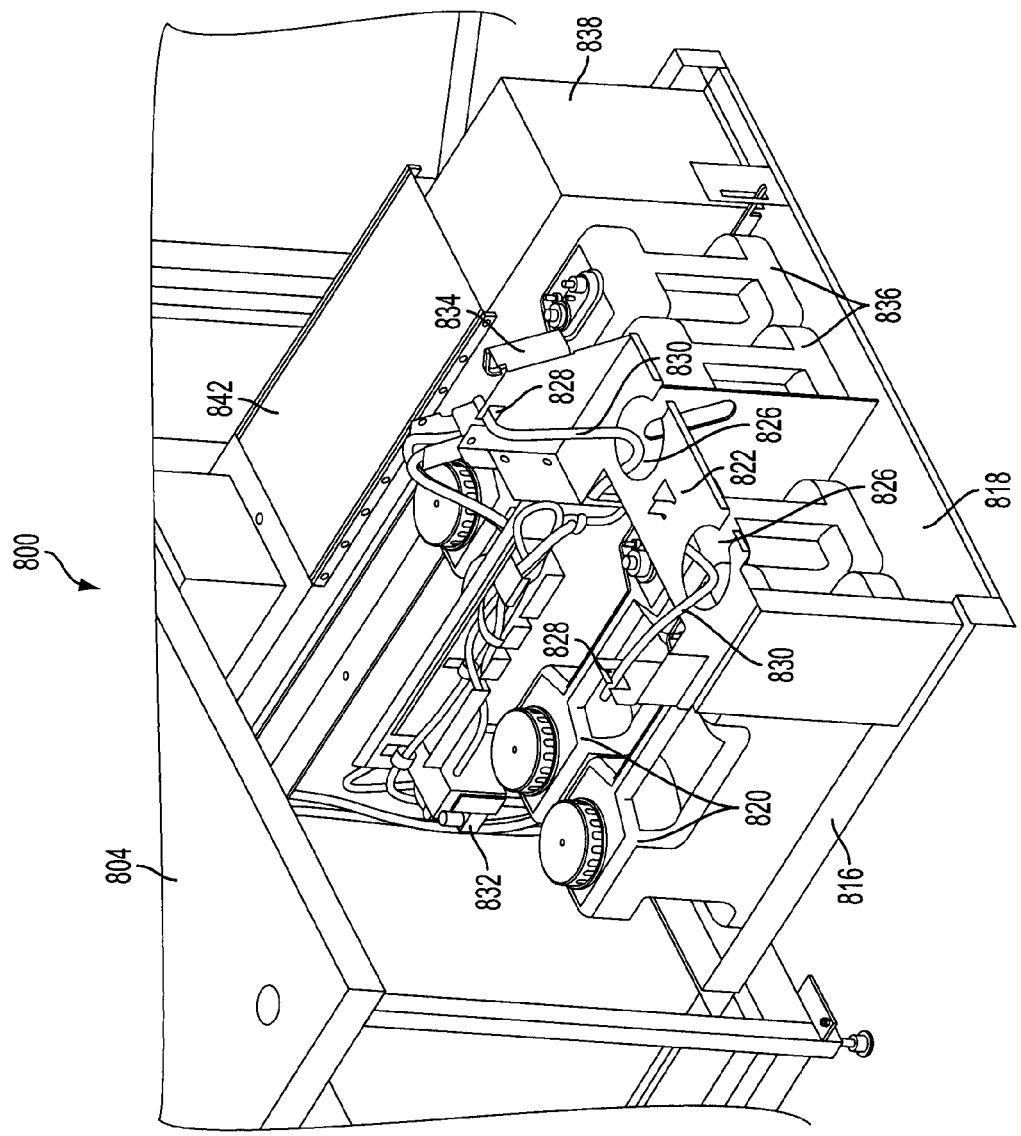

An exemplary embodiment of a cabinet for mounting the housing 124 is illustrated in FIGS. 8A and 8B. The cabinet 800 may comprise a frame 802 formed of welded box tubes, to which various panels 804 are attached to form an enclosure. The front of the cabinet 800 may be closed by one or more pivoting doors 806 having suitable closures. A space 808 may be provided in the cabinet to hold a computer processing unit (CPU), such as a typical desktop computer, and a stand 810 may be provided to hold a laptop-style CPU, a keyboard, monitor, mouse, or other accessory devices. Features may be provided on the top of the cabinet 800 to engage and hold the housing 124. Standoff bars 812 may be provided to prevent the cabinet 800 and housing 124 from being placed too close to a wall. Adjustable feet 814 are provided on the bottom of the cabinet 800, and rollers or casters may also be provided to facilitate movement.

In prior cabinet designs, the cabinet typically included one or more spaces for holding fluid bottles and waste containers. In some cases, replaceable supply bottles and containers were held on drawers, and these supplies fed into a reservoir mounted in the cabinet, but off the drawer. While functional, it could be inconvenient in such designs to access the reservoirs, and in may not be possible in these or other designs to continuously refill the reservoirs while the equipment was operating. To help alleviate these problems, the exemplary cabinet 800 may include a drawer 816 having a lower deck 818 adapted to hold fluid reservoirs 820, and an upper deck 822 adapted to hold fluid supply containers 824. In the shown embodiment, there are two fluid reservoirs 820, and two fluid supply containers 824. The reservoirs 820 and supplies 822 may hold the same fluid, or they may hold two fluid supply containers, such as a wash buffer having detergent, and a second wash buffer not having a detergent. Where the fluid supply containers 824 hold different fluids, the containers, upper deck and hoses may be color-coded, provided with unique connections or shapes, or otherwise configured to help prevent them from being attached to the wrong reservoir. The upper deck 822 may include lower openings 826 to receive outlets from the fluid supply containers 824, as well as hose hooks 828 to hold hoses 830 when the fluid supply containers 824 are not in place. One or more pumps 832 are mounted to the drawer to regulate flow from the fluid reservoirs 820 to the rest of the AS 100.

In the embodiment of FIGS. 8A and 8B, the fluid reservoirs 820 are conveniently refilled by opening the cabinet doors 806, sliding out the drawer 816 using an integrated handle 834, attaching fluid supply containers 824 to the hoses 830, mounting the fluid supply containers 824 to the upper deck 822, sliding the drawer 816 back into the cabinet 800, and closing the doors 806. Using this arrangement, the hoses connecting the supplies to the reservoirs can be relatively short because it does not need to extend from a reservoir in the housing to a supply outside the housing, which helps prevent the likelihood of crimping or catching the hose as the supply is placed in the cabinet. This arrangement also allows an operator to more easily remove, replace and check fluid levels in the reservoirs. Providing the pump or pumps in the drawer also facilitates maintenance by locating all of the working parts associated with the reservoirs in a single, accessible location.

The fluid supply containers 824 may have barcodes or other identifiers that are read as they are loaded into the cabinet 800. A CCU associated with the system may check data associated with the barcodes to ensure that the fluid supply containers 824, such as wash buffers, are valid (e.g., not expired, the proper supplies for the test being run, not previously used and consumed, etc.), calculate the number of tests that may be run with those supplies, and convey this information for use by the system or user.

The drawer 816 also may include a bay to hold one or more liquid waste containers 836. In the shown embodiment, there are two liquid waste containers 836. Each liquid waste container 836 includes a level gauge, as known in the art, to determine when the container is filled. In contrast to typical prior systems, however, a valve is used to selectively connect one waste container or the other to the AS 100, so that the container that is not being filled can be removed and emptied. This helps extend the operation time of the AS 100, without requiring a large waste container that might be difficult for the operator to remove and empty. The liquid waste containers 836 conveniently are mounted on the same drawer 816 as the fluid reservoirs 820. This arrangement provides enhanced ease of use and accessibility to all of the fluid components contained in the cabinet 800. This arrangement also allows all of the plumbing features (pumps, hose connections, valves, etc.) located in the cabinet 800 to be mounted on a single platform, which makes assembly and maintenance significantly more convenient than in conventional designs. In addition, all of the hoses leading from the drawer 816 can be collected at the drawer making it easier to bundle the hoses to route them collectively to the rest of the AS 100. Also in this arrangement, the hoses can be held collectively by a single hose retainer, such as an elastic cord or spring that holds the collected hoses up and out of the path of the drawer 816. While the foregoing arrangement is preferred, this is not required in all embodiments, and in other embodiments they may be mounted on one or more additional drawers, or simply held in the cabinet 800.

One or more solid waste containers 838 also may be mounted on the drawer 816. in the shown embodiment, the solid waste container comprises a simple bin that may be sized to receive a conventional plastic trash bag or other removable waste container. As with the liquid waste containers 836, the solid waste container 838 may be mounted on a separate drawer, or simply mounted in or beside the cabinet 800. The solid waste container 838 may be mounted below a waste passage 840 that joins a corresponding waste passage 232 (FIG. 2) or opening to receive used pipette tips or other solid waste. To facilitate continuous operation of the AS 100 even when the drawer 816 is open, a sliding cover 842 may be provided between the solid waste container 838 and the waste passage 840. The sliding cover 842 is mounted on a rack above the solid waste container 838, and stops are placed on the various parts to slide the cover 842 in place between the solid waste container 838 and the waste passage 840 when the drawer 816 is opened, and slide the cover 842 backwards out of the way when the drawer 816 is closed. When the drawer 816 is open, pipette tips and other solid waste collect in an intermediate reservoir 844 in the passage 840 above the cover 842, and when the drawer 816 is closed the collected waste falls into the solid waste container 838.

Referring now to FIGS. 2 and 3, further details of the operating components of the exemplary embodiment are disclosed. As noted above, the housing 124 generally contains the working parts of the AS 100. The first sample bay 102, second sample bay 104, control bay 106, pipette tip input 108, and reagent bay 110 may be aligned generally in a row, such as shown, so that access is provided along the front of the AS 100. The first sample bay 102 (shown empty in FIG. 2) is open to the front of the machine, and opens rearward to a traversing channel 202 that extends behind the various input areas (102, 104, 106, 108 and 110). A plate mover 204 is provided in the traversing channel 202. The plate mover 204, which may comprise any suitable robotic device or devices, is configured to move laterally and vertically within the traversing channel 202 to move the sample plates 206 (two are shown) between various processing stations. If desired, multiple plate movers or other manipulation devices may be used on other embodiments. An example of a plate mover 204 comprises a lateral movement motor 208 that moves the device along a track in the traversing channel 202, an elevator platform 210 that is mounted to the lateral movement motor and provided with a suitable elevator motor, and one or more extension sliders (not shown) that move the plates 206 onto and off of the elevator platform. Suitable traversing, elevating and sliding mechanisms are known in the art, and available from Stratec Biomedical Systems AG of Germany. The particular details of such motors, elevators and other movement equipment do not form a part of the present invention, and no further discussion of such devices is necessary here.

One or more sample preparation stations may be provided along the traversing channel 202. In the shown embodiment, a first preparation station 212 is located between the reagent bay 110 and the traversing channel 202, and a second preparation station 214 is located behind the pipette tip input area 108, and next to the control bay 106. Each preparation station 212, 214 includes a flat platform onto which a plate 206 can be placed by the plate mover 204, and may include one or more plate locks or grips adapted to hold the plate 206 against unwanted movement. The preparation stations 212, 214 may be include a heating or cooling block to elevate, decrease, or maintain the temperature of the specimens located in the plate 206. As noted above, the plates 206 may be mounted on carriers (not shown) that facilitate plate movement and handling. The plates 206 may be moved onto the sample preparation stations with such a carriage, or separately therefrom. The preparation stations are provided to hold sample plates 206 during sample preparation steps, such as reagent dispensing, aspiration, mixing and so on. For example, plates 206 at the first preparation station 212 may be processed by adding reagents, and plates 206 at the second preparation station 214 may be processed by adding controls or calibrators from the control bay 106 or by adding samples from the second sample bay 104. If desired, both preparation stations 212, 214 can be integrated into a single station. A processing station also may be used to simply hold a plate while other operations are being performed.

One or more pipettors or other devices may be mounted within the housing 124, and adapted to move through the housing 124 to perform various operations necessary to process the samples. In the shown embodiment, two four head pipettors 216 are provided. Each pipettor 216 comprises four pipetting heads, each of which may have an independent pump and control system so that they can operate independently with respect to pipetting operations. The pipettor heads are fixed relative to one another, but if desired, the pipettors 216 may comprise a so-called "varispan" arrangement, in which the width between the pipettor tips can be varied. Suitable pipettors are known in the art, and available, for example, through Stratec Biomedical Systems AG of Germany.

Where the pipettors are spaced at a fixed distance, the distance between the pipettors and the spaces between the various components and supplies may be selected to facilitate the universal use of the pipettes across the various features. For example, the pipette tips may be spaced a distance corresponding to approximately a whole multiple of (such as twice) the distance between adjacent wells on a standard 96-well plate. In this embodiment, the reagent packs may be spaced to accommodate one or two pipette tips in each reagent reservoir, the second sample containers may be spaced to each receive one pipette tip, and so on. To provide greater flexibility, the pipette tips may having separate vertical drive motors to permit them to be individually raised and lowered.

The first and second pipettors 216 each may be mounted on a guide arm 218 that runs along a lateral track 302, and lateral movement may be controlled by a number of belts 220 and one or more associated motors 304. In this embodiment, two of the belts (one at the front and one at the back of the housing 124) operate to traverse the first pipettor 216, and the remaining two belts traverse the second pipettor 216. Similarly, each pipettor 216 may be movably mounted on a longitudinal rack 222 that extends in the fore-aft direction (perpendicular to the lateral track 302), and movement in the longitudinal direction may be controlled by a machine screw 224 that is rotated by an associated motor (not shown).

In the shown exemplary embodiment, two four-head pipettors 216 may be sufficient to perform all of the desired processing steps for various different assay protocols. One pipettor 216 may be used for operations at one side of the housing 124, and the other may operate at the other side of the housing 124. In other embodiments other arrangements of single- or multiple-head pipettors may be used. For example, a single pipettor may be used, or pipettors may be mounted on different articulating systems, such as robot arms and the like. As noted before, pipette tips are stored in drawers 122, and accessed by the pipettors 216 through openings 120 through a panel over the drawers. Any suitable mechanism may be provided to connect new pipette tips to and disconnect used pipette tips from the pipettors 216. The details of the pipettor heads and tip attachment and ejection mechanisms are known in the art, and need not be described here. For convenience, a waste passage 232 may be provided in the housing 124 to provide a passage to a solid waste container 838 (FIGS. 8A and 8B) located in a cabinet 800 (FIG. 8) below the housing 124.

The exemplary AS 100 also may include an incubator station 226 adapted to receive one or more plates 206. An exemplary incubator station 226 may comprise a number of stacked incubator chambers (e.g., ten temperature-controlled plate slots) into which the plates 206 are selectively placed to perform various processing steps. One or more of the incubator chambers may include a shaker to shake the samples during incubation. To help improve assay performance, it may be desirable to shake the samples in a series of shaking and pause cycles, but this is not required. A typical shaker may have multiple configurable parameters, such as speed, upper and lower speed range, acceleration and deceleration rates, shake time, and pause time. The system may be adapted to detect and verify that shaking is being performed according to specifications. In addition, shaking in the incubator may stop when plates are being loaded in that incubator or others in the incubator stack. Suitable incubators are known in the art, and available, for example, from Stratec Biomedical Systems AG of Germany.

Next to the incubator station are one or more washing stations 228. The washing stations 228 are provided to add wash buffers to the samples and aspirate unwanted fluid. Each washing station may include a sample plate mount, which may have an integrated shaker, one or more wash buffer dispensers, and one or more aspirators. One or more magnets may be mounted on a movable magnet plate located below the sample plate mount, and the magnet plate may be selectively moved upwards towards the multi-well plate 206 to attract paramagnetic beads in the specimens. Suitable wash stations are known in the art, and available, for example, from Stratec Biomedical Systems AG of Germany.

A luminometer 230 or other test apparatus (such as a fluorometer or combined luminometer/fluorometer) may be mounted in the housing 124, such as below the pipette tip input 108. The luminometer 230 is adapted to detect a light signal that indicates the presence of one or more viral DNA strands or other signal indicia to determine the presence or absence of a virus or other condition in the patient. Suitable luminometers are known in the art, and available, for example, from Stratec Biomedical Systems AG of Germany.

The design of plate movers, pipettors, incubators, shakers, wash stations, luminometers, and other automated processing equipment is generally known in the art, and the details of such designs do not form any part of the invention. As such, these details are not described here.

It has been found that the AS 100 can be configured to provide several significant advantages over typical sample processing systems. In particular, the AS 100 includes modular components, such as reagent packs and the like, that can be replaced so that the AS 100 can process samples according to various different protocols. The exact processing steps and reagents can be selected according to the particular protocols called for by the sample, and additional processing stations may be added as necessary to accommodate additional assay steps. Existing processing stations can simple be ignored if they are not needed for a particular assay. In addition, multiple identical stations may be provided where simultaneous processing is desired.

The AS 100 also can be configured to process multiple different assays simultaneously. For example, a single multiple-well plate provided in the first sample bay 102 may include samples that require processing according to slightly different reagent mixtures, in which case the AS 100 may be programmed to deposit the required reagents in each particular well. This operation can be facilitated by creating a computer file with a map that identifies the type of sample in each plate well, associating this file with the plate using a barcode or other identifier, and reading the barcode before or while the plate is processed in the AS 100.

The exemplary AS 100 also includes first and second sample bays 102, 104 that are configured to receive samples in different formats (e.g., in different containers, in different collection media, in different stages of processing, etc.). The first sample bay 102 receives samples provided in a 96-well plate format, and the second sample bay 104 receives samples provided in individual sample containers. This arrangement has been found to be particularly useful in the context of conventional HPV testing processes. Many HPV tests are conducted on the portion of a cervical sample that remains after a pap smear test is conducted. Often, relatively little patient tissue is left in such liquid-based cytology sample containers, and it may be necessary to process the remaining sample to make it suitable for HPV testing. Typical processing steps include centrifugation of an aliquot of the remaining sample to pellet the cells, removal of the LBC medium, and processing of the cells to obtain nucleic acid samples. The resulting processed samples typically have relatively little volume, and often are collected into a sample plate having many samples from many different patients. What is left of the original sample usually is archived in case further tests are required. An automated system for preparing such nucleic acid samples in multi-well plates is described in U.S. application Ser. No. 12/588,304, which is incorporated herein by reference in its entirety. In other cases, cervical samples may be collected specifically for HPV testing (or with HPV testing being the primary test). An example of such a collection process involves the digene HPV Test Kit, which may use a cervical brush to collect a cervical sample in a vial containing the digene Collection Medium ("DCM"), both of which are available through Qiagen. The sample container 506 illustrated in FIG. 5 is one example of such a container. Samples taken specifically for HPV testing may contain a relatively large amount of testable tissue, and may be tested for HPV with relatively little pre-processing, particularly when compared to remainder samples from pap smear tests. To account for these different sample sources and formats, the first sample bay 102 may receive pre-processed cervical samples (i.e., samples that have been processed to provided purified nucleic acid which may be in a different medium than their original collection medium), and the second sample bay 104 may receive unprocessed cervical samples (i.e., samples provided in a sample collection medium).

Despite the differences between samples developed from pap smear sample remainders and samples taken specifically for HPV testing, the exemplary AS 100 is able to process both sample types. Further, the AS 100 may be configured to process both sample types simultaneously, and without interrupting the machine's operation. Providing two separate sample bays facilitates this operation by providing sample inputs configured to receive specific sample formats, but it would be possible in other embodiments to provide a single sample bay adapted to receive multiple sample formats. Multiple-format processing may, in some circumstances, provide a significant benefit over typical processing systems that rely on uniformity in the samples to operate properly and continuously. In other embodiments, further flexibility may be provided by adding more bays or adapting existing bays to receive samples in further formats. Despite the advantages possible from simultaneously processing both sample types, this ability may not be necessary where samples are provided largely in one format or the other, or where single-format machines are otherwise desired. As such, other embodiments may be configured such that there is only a single sample bay, or so that multiple sample bays receive samples in substantially the same format.

The illustrated embodiment may operate, in general terms, by consolidating specimens (i.e., patient samples and controls or calibrators, where desired) into a multi-well plate, and then processing and testing the samples collectively. Some or all of the specimens in a single plate may be provided when the plate is initially entered at the first sample bay 102. In other cases, the specimens may instead or additionally come from the individual samples provided in the second sample bay 104, or from the controls and calibrators found in the control bay 106. Specimens provided from the second sample bay 104 or control bay 106 may require additional processing before they are placed in the multi-well plate, but this is not required in all embodiments. While the many specimens in a single multi-well plate may come from various different sources, they all may be processed according to the same protocol. Alternatively, the protocols for the different samples may differ somewhat, in which case the AS 100 is programmed to track the kind of sample in each well, and treat them disparately as necessary to follow the specified protocols. For example, the pipettors 216 may dispense different reagents or different amounts of reagents in the different specimens types, or the washing stations 228 may dispense somewhat different wash buffers in each specimens type. Ultimately, all of the specimens in a single multi-well plate are tested and returned to the first sample bay 102 for removal. While the foregoing consolidation regime is believed to be helpful in at least some embodiments, in other embodiments, separate multi-well plates may be used for samples provided in the second sample bay 104 or for controls and calibrators. In still other embodiments, an AS 100 may be capable of mixing samples in a single plate, but operated so that it does not do so. This may be done, for example, where samples of only one type are available, where differences in assay protocols can not be conveniently accommodated (for example, assay differences such that a single unified protocol may be difficult to design or inefficient to run), or where samples of one type are provided in completely filled plates.

A general process flow for an embodiment may begin by querying all of the system resources to determine the kinds of samples loaded into the system and the amount of supplies available to process those samples. Next, the system may prepare a processing plan, and begin scheduling resupply instances. Where samples of two different types are available, the system may process them separately or consolidate them as processing occurs. For example, the system may fill empty wells on each multi-well plate provided in the first sample bay 102 with any available samples in the second sample bay 104. Of course, a user also may provide preferences as to how to process mixed sample supplies.

Figure 9:
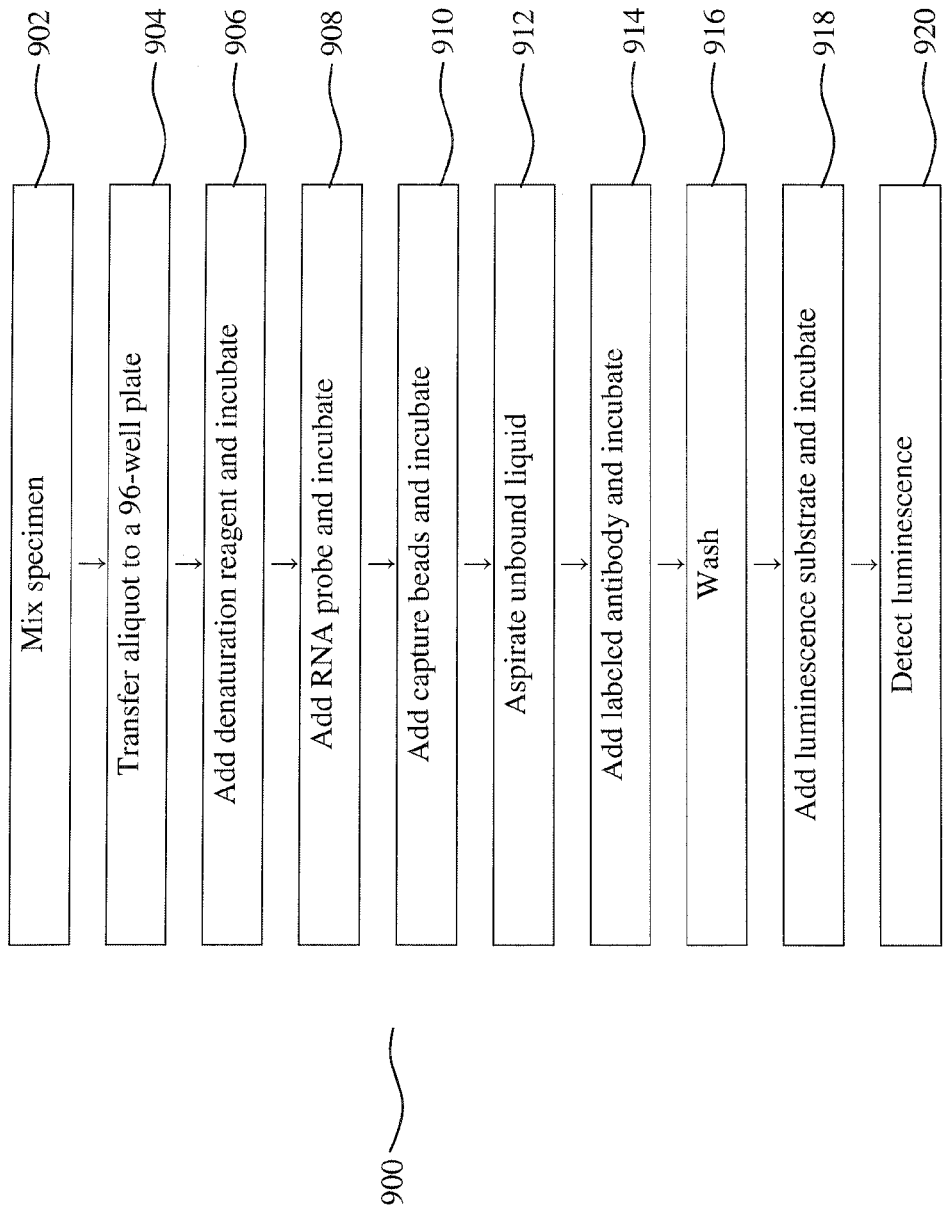
FIG. 9 is a flowchart illustrating an exemplary testing process.

An exemplary processing method is now described with respect to the flow path 900 illustrated in FIG. 9. In this embodiment, the AS 100 is equipped to perform assays to determine the presence of HPV in human cervical samples, but this use is only exemplary. The illustrated flow path begins after the machine has been loaded with sufficient samples, reagents, and other consumables to begin processing. In this example, the flow path is provided from the standpoint of specimens drawn from patient samples provided in sample containers at the second sample bay 104, but some of the specimens may be calibrators or positive and/or negative controls processed in parallel with patient samples. At step 902, the specimens are mixed by mechanical agitation of their containers, by pipetting action, or both. Mixing may be optional, depending on the type of specimen. For example, mixing may be desirable for samples comprising intact cells, or cells that have been stored in a buffer than can cause cell lysis. Also, mixing may be performed before the samples are loaded in the second sample bay 104. For example, individual samples, or multiple samples loaded in one or more sample racks, may be mounted on a shaker platform that mixes the samples (e.g., for about 2 minutes) before they are placed in the AS 100.

In step 904, the pipettor 216 transfers an aliquot of each specimen (whether it is a patient sample or a control/calibrator) to a multi-well plate 206 located at a preparation station (e.g., station 212 or station 214). The plate 206 may be positioned at the station by the plate mover 204 as part of the initial process setup, or placed manually by an operator. If the plate mover 204 is used to place the plate 206 at the processing station, the plate mover 204 may move on to perform other tasks while the plate is filled with specimens.

The multi-well plate 206 may be empty when it is placed on the station, or it may include other specimens initially provided in the multi-well plate 206 when it was installed in the first sample bay 102. Such specimens may be produced by a pre-analytical system, as described elsewhere herein. Where it is desired to process only specimens initially provided in the multi-well plate 206 (i.e., where it is not desired to process specimens taken from the second sample input 104 or control bay 106), steps 902 and 904 may be optional or omitted. Nevertheless, a mixing step may still be desired for specimens initially provided in a multi-well plate. In order to provide some redundancy and the ability to retest specimens, an additional step may be provided in which a portion of each specimen in a plate is transferred to a second multi-well plate. This may be particularly useful for samples initially provided in the plate, as it may be relatively cumbersome to obtain a duplicate of those samples if additional testing is required (additional samples can more easily be taken from the sample containers already in the second sample bay 104). While the multi-well plate 206 may be entirely filled with specimens in step 904, some wells may remain unfilled.

At step 906, the pipettor 216 draws a denaturation reagent from a reagent reservoir 702 and adds the denaturation agent to each specimen. Specimens may be provided in a collection medium comprising 1.0% NP-40, 0.25% sodium deoxycholate, 50 mM Tris-HCl, 25 mM EDTA, 150 mM NaCl, and between 0.05% and 0.09% sodium azide. The denaturation reagent may comprise, for example, for a 50 microliter sample, about 25 microliters of about 1.75 N NaOH or another denaturation reagent. Oil may be added to each well during this step and may again be added to each well after subsequent aspirations, which may prevent evaporation and promote greater temperature uniformity. The oil may be silicone oil. The oil may have a viscosity of about 5 cSt. The multi-well plate 206 is then transported by the plate mover 204 to a first position in the incubator 226, and incubated for about 30 minutes at about 70° C. with optional shaking.

At step 908, the plate mover 204 transports the multi-well plate to a sample preparation station, and the pipettor 216 withdraws an RNA probe from another one of the reagent reservoirs 702 and adds the RNA probe to each specimen. The RNA probe may be provided at concentration of about 375 ng/ml in a probe diluent. The RNA probe may comprise one or more HPV genomic sequences or a subsequences thereof, which may specifically hybridize to one or more high-risk HPV subtypes associated with elevated risk of cervical cancer, such as types 16, 18, 26, 31, 33, 35, 39, 45, 51, 52, 56, 58, 59, 66, 68, and 82, or a subset of these high-risk types, such as types 16, 18, and 45. Exemplary RNA probes comprising HPV genomic sequences are described in HPV U.S. patent application Ser. No. 12/605,605, filed Oct. 26, 2009, which is incorporated by reference herein in its entirety. The probe may be provided in a probe diluent comprising 2.2 M BES (N,N-Bis(2-hydroxyethyl)-2-aminoethanesulfonic acid), 2.6% polyacrylic acid (PAA), 0.7 N NaOH and between 0.05% and 0.09% sodium azide. Preferably the probe diluent has a viscosity that facilitates more accurate dispensing by automatic pipetting techniques, such that the desired volume can be accurately and automatically pipetted. If the viscosity is undesirably low, the probe diluent may be unable to form a stable drop; conversely, if the viscosity is undesirably high, the probe diluent drop may be too large and may cause significant disturbance of the contents already in the sample (e.g., by splashing). The plate mover 204 then moves the multi-well plate 206 to a second position in the incubator 226 where the specimens are incubated for about 22 to about 30 minutes at 69.5° C. with optional shaking.

At step 910, the plate mover 204 transports the multi-well plate 206 to a sample preparation station, where 25 microliters of capture bead suspension are added by the pipettor 216 from another reagent reservoir 702. Exemplary capture beads may be paramagnetic beads comprising polystyrene, may have a diameter of about 1 micrometer, and may be coupled to an antibody via an 1-ethyl-3-[3-dimethylaminopropyl]carbodiimide hydrochloride (EDAC) linker. Another exemplary capture bead that may be used is approximately 1 μm carboxylated SERADYN beads, available from Thermo Fisher. The capture beads also may comprise a monoclonal anti-RNA-DNA hybrid antibody derived from a hybridoma cell line is used, such as those described in U.S. Pat. Nos. 4,865,980, 4,732,847, and 4,743,535, the contents of each of which are incorporated herein by reference in their entirety. Hybrid-specific monoclonal antibodies may be prepared using techniques that are standard in the art. The hybrid-specific monoclonal antibody may be used for both capturing and detecting the target nucleic acid. The capture beads may be contained in a buffer comprising 6% casein, 100 mM Tris-HCl, 300 mM NaCl, and 0.05% sodium azide. The multi-well plate 206 is then transported by the plate mover 204 to a third position in the incubator 226 where the specimens are incubated for 30 minutes at 69.5° C. with optional shaking.

At step 912, the plate mover 204 transports the multi-well plate 206 to a wash station 228, where a plate of magnets is raised into position below the multi-well plate 206 to attract the paramagnetic beads for about 2-3 minutes, after which unbound liquid is aspirated. The wash station 228 may optionally shake the plate during the magnetic attraction and/or aspirating processes.

Next, the plate mover 204 transports the multi-well plate to a sample preparation station for step 914 in which a labeled antibody is added by the pipettor 216 from another reagent reservoir 702. The labeled antibody may comprise a monoclonal anti-RNA-DNA hybrid antibody (examples of which are described above) which may be directly or indirectly coupled to a detectable label. The labeled antibody may be provided in a buffer comprising 100 mM TrisHCl, pH 7.4, 0.5 M NaCl, 0.1 mM $ZnCl_2$, 1.0 mM $MgCl_2$, 0.25% Tween 20, 0.2 mg/ml RNase A, 4% hydroxypropyl-b-cyclodextrin (cyclodextrin), 30% bead dilution buffer as discussed previously, 0.05% goat IgG, between 0.05% and 0.09% sodium azide. The label may comprise an alkaline phosphatase. The multi-well plate 206 is then transported by the plate mover 204 to another station in the incubator 226, where in the specimens are incubated for about 30 minutes at about 45° C. with optional shaking.

At step 916, the plate mover 204 transports the multi-well plate 206 back to the wash station 228 (or to another wash station), where beads are again attracted to magnets for about 2-3 minutes, after which unbound liquid is aspirated, with optional shaking. After aspiration, a wash routine is conducted. The wash routine comprises: moving the magnets away from the multi-well plate to free the magnetic beads, adding 300 microliters of a wash solution, allowing the wash solution and beads to incubate for about 3 minutes with optional shaking, after which beads are attracted with magnets for about 2-3 minutes, and the unbound liquid is aspirated. The wash routine is carried out about two to three times with a first wash solution containing detergent, then one time with a second wash solution that is free of detergent. An exemplary first wash solution comprises 40 mM Tris, pH 8.2, 100 mM NaCl, 0.5% Triton-X 100 and between about 0.05% and about 0.09% sodium azide, and an exemplary second wash solution comprises 40 mM Tris, pH 8.2, 100 mM NaCl, and between about 0.05% and about 0.09% sodium azide.

The plate mover 204 then transports the multi-well plate 206 to a sample preparation station for step 918, in which 40 microliters of a luminescence substrate is added. Exemplary luminescence substrates include LUMI-PHOS 530 reagent (Lumigen, Detroit, Mich.), DR2 (Applied Biosystems, Foster City, Calif.), and CDP-Star® with Emerald-II™ Enhancer (a dioxetane-based substrate, available from Applied Biosystems). The multi-well plate 206 then is transported by the plate mover 204 to another station in the incubator 226 where the specimens are incubated for about 10-15 minutes at about 15-30° C. with optional shaking.

At step 920, the plate mover 204 transports the multi-well plate 206 into a luminometer 230. The luminometer evaluates the luminescence of each sample, as known in the art. Luminescence may be measured, for example, in relative luminescence units (RLUs), which may be transmitted to an on-board controller and/or to a central control unit. Luminescence values may be computationally processed to indicate the presence or absence of an analyte in the samples. For example, an HPV assay may be performed in which an assay positive standard containing 1 pg/ml of HPV DNA is used to establish the luminescence corresponding to a positive cutoff. Sample RLU values are then divided by the RLU value for the positive standard creating a RLU/CO (RLU to cutoff value). Results are reported in RLU/CO and values greater than or equal to a given threshold, such as 1.0, can be considered positive. Alternatively, ranges of RLU/CO values may be established that are considered to be negative, indeterminate, or positive. After testing, the plate mover 204 transports the multi-well plate 206 to the first sample bay 102 for removal by the operator. The first sample bay 102 may have multiple plate positions, so that several processes plates can accumulate before being unloaded.

In the foregoing embodiment, it will be understood that some specimens may be processed at the same time according to alternative assay protocols that vary from the foregoing protocols. Thus, some specimens may receive different reagents or skip reagent addition steps. However, due to the specimens all being on the same multi-well plate 206, they all will be incubated and shaken together.

In steps involving dispensing samples, controls, calibrators or reagents (e.g., steps 904, 906, 908, 910, 914, 916, and 918), a pipette tip is affixed to a pipettor, an aliquot is drawn from a sample or sufficient reagent is drawn into the pipette tip for multiple samples, the pipette tip is positioned over each a plate well and the desired volume of sample or reagent is dispensed. To prevent cross-contamination, pipette tips used for dispensing reagents do not contact any specimens during ordinary use. Where even greater control over cross-contamination is desired, a single pipette tip may be used to dispense reagent into only a single specimen, after which the pipette tip is discarded or washed and reused. Reagents also may be drawn from a reservoir into a fluid path, and dispensed from a re-useable nozzle. To prevent cross-contamination, a re-useable nozzle typically does not contact samples during ordinary use. A re-useable nozzle may be periodically washed and/or flushed to further decrease the likelihood of cross-contamination and prevent buildup of reagent residue. Dedicated aspirators, such as aspirators used in the wash stations 228, may be periodically washed in a fluid bath, or operated such that they do not need cleaning, as known in the art.

Whether the reagent dispenser is a pipette tip or nozzle, multiple channels may be used for concurrent dispensing, thereby decreasing processing time and potentially improving throughput. Multiple channels may be spaced to match the distance between adjacent plate wells, or a whole multiple of this distance, so that each dispensing pipette tip or nozzle is always positioned over a well For example, if the spacing between pipette tips or nozzles is twice the distance between wells, an 8-well row of a plate can be filled by moving the pipette tips/nozzles over four of the wells, dispensing, moving the pipette tips/nozzles over the other four wells, and dispensing. This achieves complete dispensing for each row in two dispensing steps and with very little extraneous movement.

Though this example is described with respect to particular reagents, volumes, incubation times, temperatures and processing steps, these variables and steps may be varied within the scope and spirit of the invention. For example, samples within a single multi-well plate may have different reagents added or different volumes of reagents added than other samples in the same multi-well plate. More or fewer than the steps recited in this example may be performed, and steps may be repeated, omitted, and/or replaced. Additionally, other denaturation reagents, buffers, wash solutions, probes, probe diluents, capture beads, capture bead buffers, labeled antibodies, labeled antibody buffers, luminescent substrates, incubation times, and incubation temperatures may be used, including, for example, those described in U.S. Ser. Nos. 12/605,605 or 12/605,540, and others, such as those described in Sambrook et al., Molecular Cloning: a laboratory manual, 3rd Edition Cold Spring Harbor Laboratory Press, CSH, New York, 2001; Sambrook et al., Molecular Cloning, A Laboratory Manual (2nd Ed.), Cold Spring Harbor Laboratory, Cold Spring Harbor, N.Y., 1989; Current Protocols in Molecular Biology, F. M. Ausubel et al., eds., Current Protocols, a joint venture between Greene Publishing Associates, Inc. and John Wiley & Sons, Inc., (including supplements); Ausubel et al, Short Protocols in Molecular Biology, John Wiley and Sons, 1992), each of which is incorporated by reference herein in its entirety.

As noted above, the plate mover 204 may be free to perform other processes while certain steps are being performed. In addition, some or all of the various steps of the process may be performed substantially simultaneously by providing sufficient processing stations and equipment in the housing 124. For example, one plate 206 may be filled in step 904, while another is being aspirated in one wash station 228 in step 912, while another is being washed in another wash station 228 in step 916. At the same time, several plates may be in various positions within the incubator 226, and another may be being transported between operations. Other simultaneous operations may be occurring as well. To accommodate simultaneous operation, redundant processing stations and equipment may be provided. For example, each wash station 228 may be equipped to perform either step 912 or step 916. As another example, where one process may take significantly longer than others, multiple processing stations may be provided for that process and operated on a staggered cycle to increase the frequency at which plates complete that particular process, and maintain the flow path 900 at a faster pace.

At the end of the testing process described above, a CCU associated with the AS 100 may evaluate the results to determine whether they are reliable, such as by confirming that positive and negative controls do not indicate a processing problem. The CCU also may evaluate each tested specimen to determine whether the test result is negative or positive, and store this information with the sample identification number for later use to report test results and so on.

The CCU also may determine whether any of the specimens require further testing to validate the initial test (such as by simply retesting the sample), or provide more information about the test results. For example, where an HPV test is being conducted, a first assay may use chemiluminescence for the qualitative detection of multiple high risk genotypes, and a reflex assay may determine the presence of particular genotypes. Examples of HPV assays that may be used in this manner are the digene eHR HPV DNA Test, which identifies fifteen high risk HPV genotypes (16, 18, 31, 33, 35, 39, 45, 51, 52, 56, 58, 59, 66, 68, and 82), and the digene eHR HPV 16 18/45 DNA Test, which detects the presence of genotypes 16, 18 and 45. Both of these tests are available from Qiagen, as noted above. While a full panel test may be followed by reflex testing, as described above, some samples may be reflex tested at the outset. This may be appropriate, for example, where abnormal cells are observed in a pap smear, suggesting that full panel testing can be bypassed. At the end of the above testing process 900, the CCU may query each sample's test schedule to determine whether additional testing is called for after receiving a particular result (which may be a positive result or a negative result), and identify each sample that matches the retest criteria.

The retesting process may be different for samples provided in individual sample containers in the second sample bay 104 and pre-processed specimens provided in multi-well plates in the first sample bay 102. As noted above, samples in the second sample bay 104 may comprise original samples collected primarily for the particular test being performed in the AS 100, and sufficient volume may remain in each sample container to allow subsequent testing. Thus, it may be possible to retest these original samples with relative ease. Specimens provided in multi-well plates, one the other hand, may comprise pre-processed portions of original samples that are not suitable for testing using without some processing. Furthermore, the amount provided in the multi-well plate may be insufficient for multiple tests. As such, if a retest is required for a specimen provided in a multi-well plate or other small-volume container, it may be necessary to process another specimen from the original sample container into a testable format before beginning the retest. It may be possible to avoid this additional step by generating multiple specimens from each sample, or, if the specimens in the multi-well plate have sufficient volume, removing a portion of each plate specimen to a redundant plate used for retesting. It is also envisioned that some samples initially provided as specimens in a multi-well plate may actually be testable without whatever pre-processing was used to generate the plate specimen. In such cases, retesting may be performed by simply placing the original sample container in the second sample bay 104. Also, in some cases it may be possible to recondition samples that have been processed and tested in the luminometer to be retested.

Retests may be performed in substantially the same way as the above process, but with any necessary variations to accommodate any differences between the initial test and retest protocols. In an embodiment performing HPV testing, the CCU may identify the samples requiring retesting to the operator via a graphical user interface or by a printed test result form. The operator may remove the retest samples from the second sample bay 104, mix them using a vortexer (if mixing is not done in the AS 100) and replace them in the AS 100 on one or more sample racks. For specimens provided on multi-well plates, the user may process additional retest specimens into a new multi-well plate and place them in the first sample bay 102. Where necessary, the operator also may load and mix the appropriate retest reagents, controls and calibrators into the AS 100. The samples are then processed according to the retesting protocol.

The retest protocol may include one or more retest assays. For example, in an embodiment in which samples are tested for HPV 16, 18 and 45 genotypes, a first specimen may be taken from each sample and tested for the HPV 16 genotype, and a second specimen may be taken from each sample and tested for the HPV 18 and 45 genotypes. These retests may be performed sequentially, or, if the AS 100 has sufficient equipment and resources, at the same time. In this embodiment, multiple retest specimens may be drawn separately from each sample container in the second sample bay 104, and multiple retest specimens from each sample may be provided in a multi-well plate loaded into the first sample bay 102. Of course, only a single specimen may be provided for single-assay retests, and more specimens may be provided if further tests are indicated. As with the process described earlier herein, test results may be collected and processed by a suitable CCU, and reported as necessary.

Embodiments of the AS 100 may use barcodes or other tracking systems (e.g., radio frequency identification ("RFID") chips, and the like) to assist with sample and resource tracking. For example, each sample plate 400 may be barcoded, and that barcode can associate each plate well with a particular sample in a plate "map." The sample information may include, for example, the patient's identity, the requested test protocol(s), and a history of any prior processing activities. The plate barcode may be read by a handheld scanner before it is placed in the AS 100, and scanned again by a fixed scanner inside the AS housing 124 as it is picked up from the first sample bay 102 by the plate mover 204. Similarly, each individual sample container 506 may be barcoded and associated with patient and processing information. The sample containers may be scanned before or as they are inserted into the AS 100, by a handheld scanner or a scanner located inside the second sample bay 104. As noted above, the sample rack 500 also may include barcode information. Reagents, controls and calibrators also may be barcoded to track their use, and provide a history of which reagents were used with which samples. At any time a barcode does not match expected values, the AS 100 may require user input to correct the error. For example, the AS 100 may require hand scanning for an unread barcode, or removal or replacement of a reagent or sample that is not properly loaded in the AS 100. Barcodes also may be used to ensure that samples requiring certain reagents or other processing steps are not inadvertently loaded when the AS 100 is not set up to process those samples. Additional barcode readers may be placed at various locations throughout the AS 100 to ensure quality control. For example, a barcode on a sample plate 400 may be scanned just prior to the luminometer entrance to confirm that each plate tested in the luminometer is known and accounted for. Tested plates may be rescanned a final time as they are replaced in the first sample bay 102 to record their completed processing.

In addition to tracking the presence and kind of reagents, embodiments of the AS 100 may track expiration and lot codes provided in reagent barcodes. Tracking this information permits the system to monitor the reagents to ensure that expired reagents are not used, and provide warnings before fluid supply containers need to be changed. This tracking also allows operators to use a random selection of reagents that may have different expiration dates, without having to manually track the expiration dates. Automated expiration date tracking and the ability to quickly load new reagents without interrupting operation also alleviates the need to schedule downtime to replace reagents.

It may be necessary or desirable to calibrate the AS 100 from time to time to ensure that it is working properly and within desired operating parameters. The calibration process may be performed using any suitable calibrators. As noted above, the AS 100 may include a dedicated control bay 106 into which calibrators are loaded. In this embodiment, calibration may be performed by pipetting the calibrators into empty plate wells on a plate that has samples in other wells, or adding the calibrator to an empty plate used only for calibration. Those wells are processed according to the necessary protocols, along with the remaining wells on the plate (assuming the remaining wells have samples in them). Calibrators also may be provided in a plate that is installed into the first sample bay 102, or in a sample container installed into the second sample bay 104. For example, where a pre-analytical processing system ("PAS") is used to prepare a multi-well plate with samples, that system may create a calibrator sample to help calibrate the AS 100. Additionally, the PAS may create a control sample to help determine whether the pre-analytical system and AS 100 are working within specifications.

The AS 100 may use any suitable calibration strategy. For example, the system may be calibrated at set time intervals, at set processing intervals, upon the occurrence of particular events, or according other criteria or a combination of criteria. For example, in one embodiment, calibration may be performed at the beginning of each daily shift, and whenever a new reagent pack from a new lot is introduced to the system (adding reagents from a new container that originated from the same reagent lot may not require calibration). Calibration also may be required upon the expiration of a reagent pack's in-use life, regardless of whether it is fully consumed or not. Expiration dates for reagents can be tracked using barcodes or other indicia.

In another exemplary embodiment, calibration may be performed for each multi-well plate processed by the system. In this embodiment, one or more wells should be left unfilled by the technician or PAS preparing the plate. Using per-plate calibration may help reduce the incidence of failed sample tests (i.e., tests performed while the machine was not within calibration specifications), but may reduce overall efficiency by taking up plate resources. However, where the plates are prepared by a PAS, the PAS may be programmed to leave empty wells on each plate to permit the AS 100 to calibrate whenever necessary without having to use a dedicated calibration plate.

In addition to calibration, the AS 100 may include a control regime to help ensure quality control and detect contamination. For example, positive controls may be used to monitor assay performance, and negative controls may be used to detect well-to-well or cross-contamination. Where the AS 100 is adapted to process samples using different collection media or pre-processing steps, it may be necessary to include multiple positive or negative controls corresponding to each sample condition. For example, samples arriving in a multi-well plate in the first sample bay 102 may include a mixture of samples extracted from different liquid based cytology media (e.g., SurePath™ samples as known and available from BD Diagnostics of Burlington, N.C. and PreservCyt™ samples as known and available from Hologic Inc. of Marlborough, Mass.), in which different controls may be used on the plate to ensure accuracy with respect to both kinds of sample. Alternatively, a single control may be used for a number of different sample types, as dictated by the circumstances. Controls may be provided in the control bay 106 or the second sample bay 104, as described above, or they may be added to a multi-well plate before it is installed in the AS 100. For example, a PAS could add any necessary controls.

Embodiments of an AS 100 may be operated substantially continuously for relatively long periods to provide ultra-high fully automated throughput. As explained and illustrated above, the system may include multiple redundant inputs to receive first and second sample types, as well as multiple redundant pipette tip supplies, reagent packs, and control/calibration/oil cartridges. The system also includes redundant waste fluid receptacles and a solid waste receptacle with an intermediate chamber that can collect waste even when the main receptacle is being emptied. Thus, each consumable or processed component can be removed and replaced while a redundant system or component is operating. As such, the system may be fully-automated and operable continuously for as long samples and supplies are being provided. The system also may include features such as automated reagent mixing and pierceable containers to reduce manual labor to virtually nil.

In one exemplary embodiment, an AS 100 was prepared to operate in a fully-automated mode to perform HPV tests on samples provided in Qiagen DCM collection tubes that were directly loaded into the second sample bay 104, and up to fifteen plates (having up to 1440 samples) processed from liquid based cytology media loaded into the first sample bay 102. The AS 100 fully automated all steps from reagent and sample loading to the final data acquisition. The assay time to the first result was reduced at least by 40% compared to manually performing the HC2® HPV DNA Test from Qiagen. The AS 100 detected up to fifteen different high risk HPV genotypes, and had an analytical sensitivity of 1875 copies (95% CI 1615-2290) of HPV 16 plasmid. Assay specificity was evaluated with 13 HPV low risk types. All HPV low risk types were tested at a high concentration of $2\times10^8$ copies/ml, and there were no false positive results. The assay reproducibility on the AS 100 was significantly improved over the manual assay using HPV 16 plasmids. The fully automated assay achieved consistent performance within plate, from plate to plate, day to day and instrument to instrument. No indication of target carryover was found when samples containing up to $10^9$ copies/ml of HPV DNA type 16 were processed on the exemplary AS 100.

The above example may be operated to provided extremely high throughput. As many as 5,000 or more assays of a single type can be run in a single day. Alternatively, the it may be possible to reconfigure such an embodiment (e.g., by simply loading the appropriate reagents), to simultaneously or consecutively run ten to twelve different assays, with 25-30 tests being conducted according to each assay every day. If necessary the reagent or sample bays may be modified to hold the necessary reagents and samples. The ultra-high output of these exemplary embodiments is also particularly beneficial considering the relatively small size of the apparatus. When measured in output per square foot of floor space, the throughput is particularly high. Nevertheless, while high out put may be obtained using embodiments of the invention, it is not required in all embodiments, and many benefits and advantages may be available even in small-scale or low output embodiments.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

We claim:

1. A reagent cabinet for an automated processing apparatus, the reagent cabinet comprising:
   a housing;
   a drawer slidably mounted in the housing and movable between a first position in which the drawer is contained within the housing, and a second position in which at least a portion of the drawer is outside the housing, the drawer having a lower deck adapted to receive a fluid reservoir, and an upper deck located above the lower deck and configured to receive a fluid supply container, the fluid supply container being selectively removable from the drawer independently of the fluid reservoir;
   a supply connection hose configured to connect the fluid supply container to the fluid reservoir; and
   a reservoir connection hose adapted to selectively connect to the fluid reservoir and to convey fluid from the fluid reservoir to a downstream location outside the cabinet.

2. The reagent cabinet of claim 1, further comprising one or more doors pivotally mounted on the cabinet and configured to close the cabinet when the drawer is in the first position.

3. The reagent cabinet of claim 1, wherein the upper deck is configured to receive a supplemental fluid supply container.

4. The reagent cabinet of claim 3, wherein the fluid supply container and the supplemental fluid supply container contain the same kind of fluid.

5. The reagent cabinet of claim 3, wherein the fluid supply container and the supplemental fluid supply container contain different kinds of fluid.

6. The reagent cabinet of claim 4, wherein the fluid supply container contains a wash buffer having a detergent, and the supplemental fluid supply container contains a wash buffer not having a detergent.

7. The reagent cabinet of claim 1, wherein the upper deck comprises a lower opening configured to receive an outlet from the fluid supply container.

8. The reagent cabinet of claim 1, wherein the upper deck comprises a hose hook configured to hold the supply connection hose when the fluid supply container is not in place on the upper deck.

9. The reagent cabinet of claim 1, wherein the fluid supply container is removable in a vertical direction from the upper deck when the drawer is in the second position.

10. The reagent cabinet of claim 1, further comprising a pump configured to convey fluid through the reservoir connection hose and to the downstream location.

11. The reagent cabinet of claim 10, wherein the pump is mounted on the drawer.

12. A reagent cabinet for an automated processing apparatus, the reagent cabinet comprising:
    a housing having a front opening;
    a drawer slidably mounted in the housing and movable in a sliding direction between a first position in which the drawer is contained within the housing, and a second position in which at least a portion of the drawer extends outside the front opening of the housing, the drawer being configured to hold one or more fluid reservoirs in a first vertical height, and to hold one or more fluid supply containers in a second vertical height, the second vertical height being higher than the first vertical height; and
    one or more supply connection hoses each being configured to connect a respective fluid supply container to a respective fluid reservoir;
    wherein the one or more fluid supply containers are selectively removable from the drawer independently of the one or more fluid reservoirs to thereby permit replacement of the one or more fluid supply containers without removing the one or more fluid reservoirs.

13. The reagent cabinet of claim 12, wherein the drawer comprises a first deck configured to hold the one or more fluid reservoirs at the first vertical height, and a second deck configured to hold the one or more fluid supply containers at the second vertical height.

14. The reagent cabinet of claim 13, wherein the second deck is positioned directly above the first deck.

15. The reagent cabinet of claim 13, wherein the first deck and the second deck are aligned in the sliding direction.

16. The reagent cabinet of claim 15, wherein the first deck and the second deck are positioned such that the one or more fluid supply containers are closer to the front opening of the housing than the one or more fluid reservoirs when the drawer is in the first position, and the one or more fluid supply containers are further from the front opening of the housing than the one or more fluid reservoirs when the drawer is in the second position.

17. The reagent cabinet of claim 12, wherein the one or more fluid supply containers comprises a plurality of fluid supply containers containing the same kind of fluid.

18. The reagent cabinet of claim 12, wherein the one or more fluid supply containers comprises a plurality of fluid supply containers containing different kinds of fluid.

19. The reagent cabinet of claim 18, wherein at least a first fluid supply container contains a wash buffer having a detergent, and at least a second fluid supply container contains a wash buffer not having a detergent.

* * * * *